(12) United States Patent
Garvey et al.

(10) Patent No.: US 6,514,934 B1
(45) Date of Patent: *Feb. 4, 2003

(54) IMIDAZOLINE α-ADRENERGIC RECEPTOR ANTAGONIST COMPOUNDS IN COMBINATION WITH NITRIC OXIDE DONORS, COMPOSITIONS AND METHODS OF USE

(75) Inventors: David S. Garvey, Dover, MA (US); Joseph D. Schroeder, Boston, MA (US); Inigo Saenz de Tejada, Madrid (ES)

(73) Assignee: NitroMed, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/280,540

(22) Filed: Mar. 30, 1999

Related U.S. Application Data

(60) Division of application No. 09/145,143, filed on Sep. 1, 1998, now Pat. No. 6,294,517, and a continuation-in-part of application No. PCT/US97/01294, filed on Jan. 28, 1997, which is a continuation-in-part of application No. 08/714,313, filed on Sep. 18, 1996, now Pat. No. 5,994,294, which is a continuation-in-part of application No. 08/595,732, filed on Feb. 2, 1996.

(51) Int. Cl.$^7$ ................................ A61K 38/00; C07K 5/06
(52) U.S. Cl. ................................ 514/2; 514/248; 514/242; 514/280; 514/307; 514/396; 514/400; 514/471; 514/18; 514/509; 514/523; 514/532; 514/649; 514/684; 514/929; 536/26.1; 424/85.1; 424/130.1; 548/335.1; 562/560
(58) Field of Search ............................ 514/2, 18, 242, 514/248, 280, 307, 400, 471, 509, 523, 532, 396, 649, 684, 929; 536/26.1; 424/130.1, 85.1; 548/335.1; 562/560

(56) References Cited

U.S. PATENT DOCUMENTS

| | | | | |
|---|---|---|---|---|
| 4,127,118 A | | 11/1978 | Latorre | 128/79 |
| 4,801,587 A | | 1/1989 | Voss et al. | 514/248 |
| 4,885,173 A | | 12/1989 | Stanley et al. | 424/440 |
| 5,059,603 A | | 10/1991 | Rubin | 514/204 |
| 5,145,852 A | | 9/1992 | Virag | 514/253 |
| 5,190,967 A | | 3/1993 | Riley | 514/411 |
| 5,236,904 A | | 8/1993 | Gerstenberg et al. | 514/12 |
| 5,256,652 A | | 10/1993 | El-Rashidy | 514/58 |
| 5,380,758 A | | 1/1995 | Stamler et al. | 514/562 |
| 5,399,581 A | | 3/1995 | Laragh | 514/396 |
| 5,439,938 A | | 8/1995 | Snyder et al. | 514/545 |
| 5,447,912 A | | 9/1995 | Gerstenberg et al. | 514/12 |
| 5,474,535 A | | 12/1995 | Place et al. | 604/60 |
| 5,492,911 A | | 2/1996 | Stief | 514/252 |
| 5,543,430 A | | 8/1996 | Kaesemeyer | 514/565 |
| 5,565,466 A | | 10/1996 | Gioco et al. | |
| 5,567,706 A | | 10/1996 | Gavras | 514/280 |
| 5,574,068 A | | 11/1996 | Stamler et al. | 514/562 |
| 5,583,144 A | | 12/1996 | Kral | 514/321 |
| 5,593,876 A | | 1/1997 | Stamler et al. | 435/188 |
| 5,612,314 A | | 3/1997 | Stamler et al. | 514/13 |
| 5,646,181 A | | 7/1997 | Fung et al. | 514/506 |
| 5,648,393 A | | 7/1997 | Stamler et al. | |
| 5,698,589 A | | 12/1997 | Allen | 514/509 |
| 5,731,339 A | | 3/1998 | Lowrey | 514/400 |
| 5,767,160 A | | 6/1998 | Kaesemeyer | 514/565 |
| 5,773,457 A | | 6/1998 | Nahoum | 514/397 |
| 5,789,442 A | | 8/1998 | Garfield et al. | 514/561 |
| 5,877,216 A | | 3/1999 | Place et al. | 514/573 |
| 5,952,361 A | * | 9/1999 | Dias Nahoum | 514/396 |
| 6,277,884 B1 | * | 8/2001 | De Tejada | 514/565 |

FOREIGN PATENT DOCUMENTS

| | | |
|---|---|---|
| EP | 0346297 | 12/1989 |
| EP | 0357581 | 3/1990 |
| EP | 0432199 | 6/1991 |
| EP | 0611248 | 8/1994 |
| FR | 2547501 | 12/1984 |
| JP | 8026962 | 1/1998 |
| WO | 9312068 | 6/1993 |
| WO | 9505172 | 2/1995 |
| WO | 9505188 | 2/1995 |
| WO | 9901132 | 1/1999 |

OTHER PUBLICATIONS

Gould et al, *Angiology*, 32(9):595–600 (1981).
Miyamoto et al, *Arnzeim.–Forsch./Drug Res.*, vol. 41(II), No. 12, pp. 1216–1221 (1991).
Krane et al, *New England Journal of Medicine*, 321(24):1648–1659 (1989).
Sonda et al, *Journal of Sex & Marital Therapy*, 16(1):15–21 (1990).
Zorgniotti et al, *Int. J. Impotence Res.*, 6:33–36 (1994).
Trigo–Rocha et al, *Neurourology and Urodynamics*, 13:71–80 (1994).

\* cited by examiner

*Primary Examiner*—Bennett Celsa
(74) *Attorney, Agent, or Firm*—Hale and Dorr LLP

(57) ABSTRACT

The present invention is directed to nitrosated or nitrosylated α-adrenergic receptor antagonists, compositions comprising α-adrenergic receptor antagonists that are optionally substituted with at least one NO or $NO_2$ moiety and compounds that donate, transfer or release nitric oxide or elevate levels of endogenous endothelium-derived relaxing factor, and methods for treating sexual dysfunctions in males and females.

50 Claims, 7 Drawing Sheets

IMIDAZOLINE α-ADRENERGIC RECEPTOR ANTAGONIST COMPOUNDS IN COMBINATION WITH NITRIC OXIDE DONORS, COMPOSITIONS AND METHODS OF USE

RELATED APPLICATIONS

This is a divisional of application Ser. No. 09/145,143, filed Sep. 1, 1998, now U.S. Pat. No. 6,294,517, which is a continuation-in-part of U.S. application Ser. No. 08/714,313, filed Sep. 18, 1996 issued as U.S. Pat. No. 5,994,294, which is a continuation-in-part of U.S. application Ser. No. 08/595,732, filed Feb. 2, 1996 issued as U.S. Pat. No. 5,932,538; and is a continuation-in-part of PCT/US97/01294, filed Jan. 28, 1997.

FIELD OF THE INVENTION

This invention generally relates to nitrosated and/or nitrosylated α-adrenergic receptor antagonists, compositions containing them and their use in treating sexual dysfunctions.

BACKGROUND OF THE INVENTION

Adequate sexual function is a complex interaction of hormonal events and psychosocial relationships. There are four stages to sexual response as described in the *International Journal of Gynecology & Obstetrics,* 51(3):265–277 (1995). The first stage of sexual response is desire. The second stage of sexual response is arousal. Both physical and emotional stimulation may lead to breast and genital vasodilation and clitoral engorgement (vasocongestion). In the female, dilation and engorgement of the blood vessels in the labia and tissue surrounding the vagina produce the "orgasmic platform," an area at the distal third of the vagina where blood becomes sequestered. Localized perivaginal swelling and vaginal lubrication make up the changes in this stage of sexual response. Subsequently, ballooning of the proximal portion of the vagina and elevation of the uterus occurs. In the male, vasodilation of the cavernosal arteries and closure of the venous channels that drain the penis produce an erection. The third stage of sexual response is orgasm, while the fourth stage is resolution. Interruption or absence of any of the stages of the sexual response cycle can result in sexual dysfunction. One study found that 35% of males and 42% of females reported some form of sexual dysfunction. Read et al, *J. Public Health Med.,* 19(4):387–391 (1997).

In both pre-menopausal and menopausal females, sexual dysfunction can include, for example, sexual pain disorders, sexual desire disorders, sexual arousal dysfunction, orgasmic dysfunction, dyspareunia, and vaginismus. Sexual dysfunction can be caused, for example, by pregnancy, menopause, cancer, pelvic surgery, chronic medical illness or medications.

In males, erectile dysfunction or impotence is thought to affect about 10% to 15% percent of adult men. Some pharmacological methods of treatment are available, however, such methods have not proven to be highly satisfactory or without potentially severe side-effects. Papaverine is now widely used to treat impotence. Papaverine is generally effective in cases where the dysfunction is psychogenic or neurogenic and where severe atherosclerosis is not involved. Injection of papaverine, a smooth muscle relaxant, or phenoxybenzamine, a non-specific antagonist and hypotensive, into a corpus cavernosum has been found to cause an erection sufficient for vaginal penetration, however, these treatments are not without the serious and often painful side effect of priapism. Also, in cases where severe atherosclerosis is not a cause of the dysfunction, intracavernosal injection of phentolamine, an α-adrenergic antagonist, is used. As an alternative or, in some cases, as an adjunct to α-adrenergic blockade, prostaglandin E1 (PGE1) has been administered via intracavernosal injection. A major side effect frequently associated with intracorprally delivered PGE1 is penile pain and burning.

Thus, there is a need in the art for treatments of male and female sexual dysfunctions, including treatments without the undesirable side effects of those agents currently used. The present invention is directed to these, as well as other, important ends.

SUMMARY OF THE INVENTION

Nitric oxide (NO) and NO donors have been recognized as mediators of nonvascular smooth muscle relaxation. As described herein, this effect includes the dilation of the corpus cavernosum smooth muscle, an event involved in the sexual response process for both males and females. However, the effects of NO and NO donor compounds together with α-adrenergic receptor antagonists or the modifications of α-adrenergic receptor antagonists to be directly or indirectly linked with a nitric oxide adduct have not been investigated.

In arriving at the present invention it was recognized that the risk of toxicities and adverse effects that are associated with high doses of α-adrenergic receptor antagonists can be avoided by the use of such α-adrenergic receptor antagonists when nitrosated or nitrosylated or when administered in conjunction with one or more compounds that donate, release or transfer nitric oxide or that elevate endogenous levels of endothelium-derived relaxing factor (EDRF). Such toxicities and adverse effects include postural hypotension, reflex tachycardia and other arrhythmias, syncope and, with respect to the ergot alkaloids, nausea and vomiting and, upon prolonged or excessive administration, vascular insufficiency and gangrene of the extremities. The α-adrenergic receptor antagonists and compounds that donate, release or transfer nitric oxide or elevate endogenous levels of EDRF work together to permit the same efficacy with lower doses of the α-adrenergic receptor antagonists.

Accordingly, in one aspect the invention provides novel nitrosated and/or nitrosylated α-adrenergic receptor antagonists: $NO_n$-α-antagonists where n is 1 or 2. The α-adrenergic antagonists can be nitrosylated or nitrosated through sites such as oxygen (hydroxyl condensation), sulfur (sulfhydryl condensation), carbon and nitrogen. The invention also provides compositions comprising one or more of such compounds in a pharmaceutically acceptable carrier.

In another aspect, the invention provides compositions comprising a therapeutically effective amount of one or more α-adrenergic receptor antagonists (α-antagonist), that are optionally substituted with at least one NO or $NO_2$ moiety, and one or more compounds that donate, transfer or release nitric oxide as a charged species, i.e., nitrosonium ($NO^+$) or nitroxyl ($NO^-$), or as the neutral species, nitric oxide (NO•), preferably in a one to ten fold molar excess, or one or more compounds that elevate levels of endogenous endothelium-derived relaxing factor (EDRF), preferably in a one to ten fold molar excess. The invention also provides compositions comprising one or more of such compounds in a pharmaceutically acceptable carrier. The α-adrenergic receptor antagonists used in the composition can be those described above and others which are known, and can alternatively be such α-antagonists which have been nitrosated or nitrosylated in accordance with the invention.

In another aspect, the invention provides methods for treating sexual dysfunctions or enhancing sexual responses in humans, including males and females, comprising administering to an individual in need thereof a therapeutically effective amount of at least one nitrosated or nitrosylated α-antagonist.

In another aspect, the invention provides methods for treating sexual dysfunctions or enhancing sexual responses in humans, including males and females, comprising administering to an individual in need thereof compositions comprising a therapeutically effective amount of at least one α-antagonist that is optionally substituted with at least one NO or $NO_2$ moiety, and at least one compound that donates, transfers or releases nitric oxide as a charged species, i.e., nitrosonium ($NO^+$) or nitroxyl ($NO^-$), or as the neutral species, nitric oxide (NO•), and/or at least one compound that elevates levels of endogenous EDRF. The α-antagonist or α-antagonist directly or indirectly linked to at least one NO or $NO_2$ group, and nitric oxide donor can be administered separately or as components of the same composition.

DETAILED DESCRIPTION OF THE INVENTION

Figure 1:
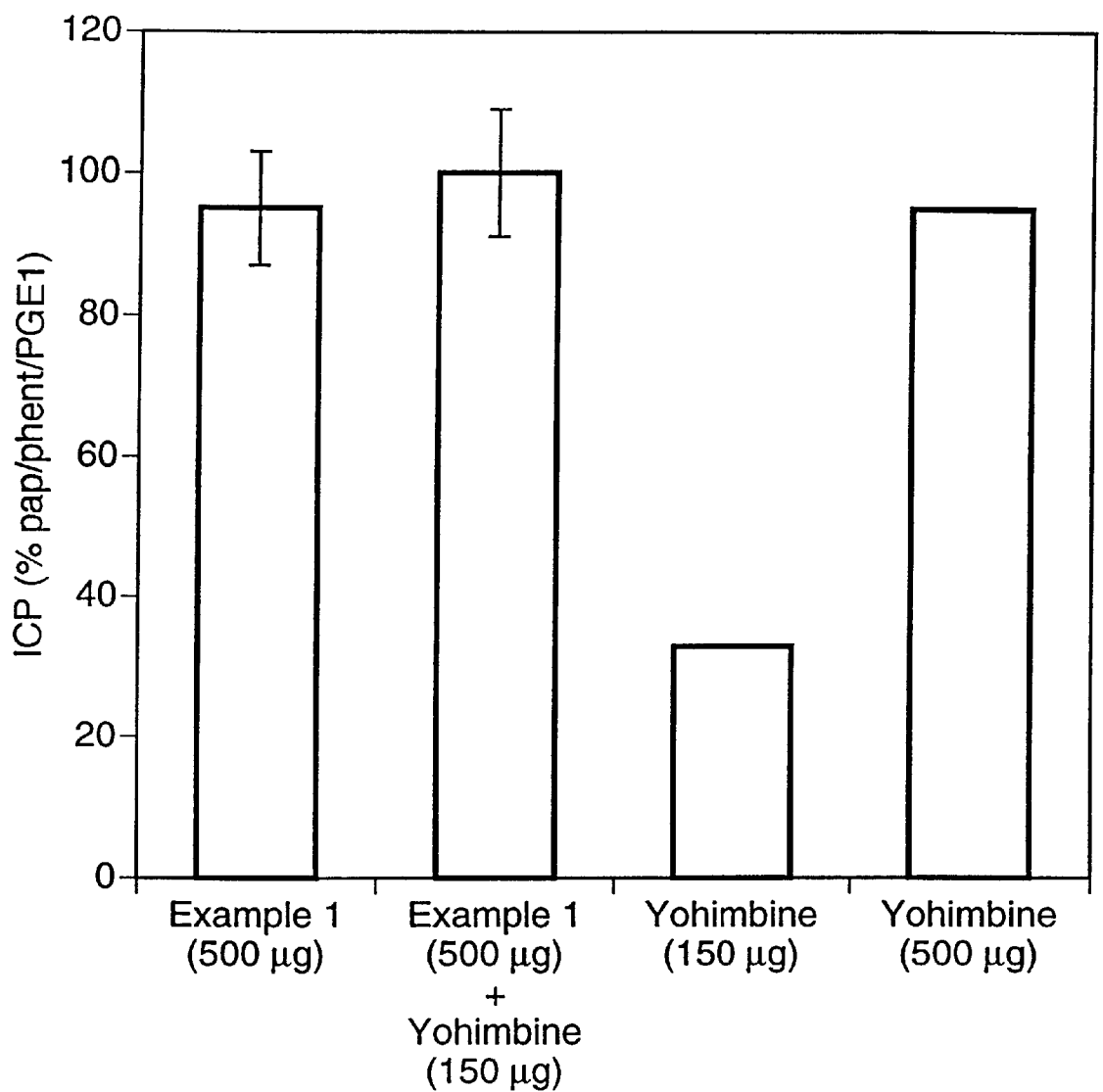
FIG. 1 shows the percent peak erectile response in vivo compared to that produced by 150 μl of pap/phent/PGE1 (30 mg/ml: 1 mg/ml: 10 μg/ml) in the anesthetized rabbit following the intracavernosal injection of 150 μl of yohimbine (150 μg, 500 μg), Example 1 (500 μg), and a combination of yohimbine (150 μg) and Example 1 (500 μg). The ordinate is the percent response of intracavernosal pressure relative to that produced by pap/phent/PGE1 and the abscissa indicates the various drugs given.

The following definitions may be used throughout the specification.

The term "lower alkyl" as used herein refers to branched or straight chain alkyl groups comprising one to ten carbon atoms, including, for example, methyl, ethyl, propyl, isopropyl, n-butyl, t-butyl, neopentyl and the like.

The term "alkoxy" as used herein refers to $R_{50}O$— wherein $R_{50}$ is a lower alkyl group as defined above. Representative examples of alkoxy groups include methoxy, ethoxy, t-butoxy and the like.

The term "alkoxyalkyl" as used herein refers to an alkoxy group as previously defined appended to an alkyl group as previously defined. Examples of alkoxyalkyl groups include, but are not limited to, methoxymethyl, methoxyethyl, isopropoxymethyl and the like.

The term "hydroxy" as used herein refers to 13 OH.

The term "hydroxyalkyl" as used herein refers to a hydroxy group as previously defined appended to an alkyl group as previously defined.

The term "alkenyl" as used herein refers to a branched or straight chain $C_2$–$C_{10}$ hydrocarbon which also comprises one or more carbon-carbon double bonds.

The term "amino" as used herein refers to —$NH_2$.

The term "carboxy" as used herein refers to —C(O)O—.

The term "nitrate" as used herein refers to —O—$NO_2$.

The term "amido" as used herein refers to —C(O)NH—.

The term "alkylamino" as used herein refers to $R_{11}$NH— wherein $R_{11}$ is a lower alkyl group. Alkylamino groups include, for example, methylamino, ethylamino, butylamino, and the like.

The term "alkylamido" as used herein refers to —C(O)$NR_{11}$— wherein $R_{11}$ is as defined above.

The term "dialkylamino" as used herein refers to $R_{12}R_{13}$N— wherein $R_{12}$ and $R_{13}$ are independently a lower alkyl group as defined above. Dialkylamino groups include, for example, dimethylamino, diethylamino, methyl propylamino and the like.

The term "nitro" as used herein refers to the group —$NO_2$ and "nitrosated" refers to compounds that have been substituted therewith.

The term "nitroso" as used herein refers to the group —NO and "nitrosylated" refers to compounds that have been substituted therewith.

The term "aryl" as used herein refers to a mono- or bi-cyclic carbocyclic ring system having one or two aromatic rings including, but not limited to, phenyl, naphthyl, tetrahydronaphthyl, indanyl, indenyl, and the like. Aryl groups (including bicyclic aryl groups) can be unsubstituted or substituted with one, two or three substituents independently selected from lower alkyl, haloalkyl, alkoxy, amino, alkylamino, dialkylamino, hydroxy, halo, and nitro. In addition, substituted aryl groups include tetrafluorophenyl and pentafluorophenyl.

The term "arylalkyl" as used herein refers to a lower alkyl radical to which is appended an aryl group. Representative arylalkyl groups include, for example, benzyl, phenylethyl, hydroxybenzyl, fluorobenzyl, fluorophenylethyl and the like.

The term "cycloalkyl" as used herein refers to an alicyclic group comprising from about 3 to about 7 carbon atoms including, but not limited to, cyclopropyl, cyclobutyl, cyclopentyl, cyclohexyl and the like.

The term "halogen" or "halo" as used herein refers to I, Br, Cl, or F. The term "haloalkyl" as used herein refers to a lower alkyl radical, as defined above, bearing at least one halogen substituent. Haloalkyl groups include, for example, chloromethyl, fluoroethyl, trifluoromethyl and the like.

The term "heteroaryl" as used herein refers to a mono- or bi-cyclic ring system containing one or two aromatic rings and containing at least one nitrogen, oxygen, or sulfur atom in an aromatic ring. Heteroaryl groups (including bicyclic heteroaryl groups) can be unsubstituted or substituted with one, two or three substituents independently selected from lower alkyl, haloalkyl, alkoxy, amino, alkylamino, dialkylamino, hydroxy, halo and nitro. Heteroaryl groups include, for example, pyridine, pyrazine, pyrimidine, pyridazine, pyrazole, triazole, thiazole, isothiazole, benzothiazole, benzoxazole, thiadiazole, oxazole, pyrrole, imidazole, isoxazole and the like.

The term "heterocyclic ring" refers to any 3-, 4-, 5-, 6-, or 7-membered nonaromatic ring containing at least one nitrogen atom, oxygen atom, or sulfur atom which is bonded to an atom which is not part of the heterocyclic ring.

The term "arylheterocyclic ring" as used herein refers to a bi- or tri-cyclic ring comprised of an aryl ring as previously defined appended via two adjacent carbon atoms of the aryl group to a heterocyclic ring as previously defined.

The term "heterocyclic compounds" as used herein refers to mono- and poly-cyclic compounds containing at least one heteroaryl or heterocyclic ring.

The term "bridged cycloalkyl" as used herein refers to two or more cycloalkyl radicals fused via adjacent or non-adjacent carbon atoms, including, for example, adamantyl and decahydronapthyl.

The term "carbonyl" as used herein refers to —C(O)—.

The term "carboxylic acid" as used herein refers to —C(O)OH.

The term "carboxylic ester" as used herein refers to —C(O)OR$_{50}$, wherein R$_{50}$ is a lower alkyl group as defined herein.

The term "phosphoryl" as used herein refers to —P(R$_{70}$)(R$_{71}$), wherein R$_{70}$ is a lone pair of electrons, sulfur or oxygen and R$_{71}$ is independently a hydrogen, a lower alkyl, an alkoxy, an alkylamino, a hydroxy or an aryl.

The term "sexual dysfunction" generally includes any sexual dysfunction in an animal, preferably a mammal, more preferably a human. The animal can be male or female. Sexual dysfunction may include, for example, sexual desire disorders, sexual arousal disorders, orgasmic disorders and sexual pain disorders. Female sexual dysfunction refers to any female sexual dysfunction including, for example, sexual desire dysfunction, sexual arousal dysfunction, orgasmic dysfunction, sexual pain disorders, dyspareunia, and vaginismus. The female may be pre-menopausal or menopausal. Male sexual dysfunction refers to any male sexual dysfunction including, for example, male erectile dysfunction and impotence.

While there are obvious differences in the sexual response between males and females, one common aspect of the sexual response is the erectile response. As described in U.S. Pat. No. 5,565,466, the disclosure of which is incorporated herein by reference in its entirety, the erectile response in both males and females is the result of engorgement of the erectile tissues of the genitalia with blood caused by the relaxation of smooth muscles in the arteries serving the genitalia.

The vasculature which serves erectile tissue in males and females is similar. In particular, the arterial circulation of the erectile tissues of the genitalia derives from the common iliac artery which branches from the abdominal aorta. The common iliac artery bifurcates into the internal and external iliac arteries. The internal pudic artery arises from the smaller of two terminal branches of the anterior trunk of the internal iliac artery. In the female, the internal pudic artery branches into the superficial perineal artery which supplies the labia pudenda. The internal pudic artery also branches into the artery of the bulb which supplies the bulbi vestibuli and the erectile tissue of the vagina. The artery of the corpus cavernosum, another branch of the internal pudic artery supplies the cavernous body of the clitoris. Still another branch of the internal pudic artery is the arteria dorsalis clitoridis which supplies the dorsum of the clitoris and terminates in the glans and membranous folds surrounding the clitoris which correspond to the prepuce of the male.

In the male, the internal pudic artery branches into the dorsal artery of the penis (which itself branches into a left and right branch) and the artery of the corpus cavernosum, all of which supply blood to the corpus cavernosum. The dorsal artery of the penis is analogous to the artery dorsalis clitoridis in the female, while the artery of the corpus cavernosum in the male is analogous to the artery of the same name in the female.

The male erectile response is regulated by the autonomic nervous system which controls blood flow to the penis via the interaction of peripheral nerves associated with the arterial vessels in and around the corpus cavernosum. In the non-aroused or non-erect state, the arteries serving the corpus cavernosum are maintained in a relatively constricted state, thereby limiting the blood flow to the corpus cavernosum. In the aroused state, the smooth muscles associated with the arteries relax and blood flow to the corpus cavernosum greatly increases, causing expansion and rigidity of the penis. Smooth muscle contraction opens valves through which blood can flow from the corpus cavernosum into the extracavernosal veins. When the relevant smooth muscles relax, the valves close diminishing venous outflow from the corpus cavernosum. When accompanied by increased arterial blood flow into the corpus cavernosum, this results in engorgement of the corpus cavernosum and an erection.

The pre-orgasmic sexual response in females can be broken down into distinct phases. Both the excitement phase and the plateau phase involve vasodilation and engorgement (vasocongestion) of the genitalia with arterial blood in a manner analogous to the male erectile response.

The excitement phase of the female sexual response is characterized by vasocongestion in the walls of the vagina which leads to the transudation of vaginal fluids and vaginal lubrication. Further, the inner one-third of the vaginal barrel expands and the cervix and the body of the uterus become elevated. This is accompanied by the flattening and elevation of the labia majora and an increase in clitoral size.

The plateau phase follows the excitement phase in the female sexual response and is characterized by prominent vasocongestion in the outer one-third of the vagina, causing a narrowing of the opening of the vagina and a retraction of the shaft and the glans of the clitoris against the symphysis pubis. These responses are also accompanied by a marked vasocongestion of the labia.

The vasocongestive aspects of the female sexual response are not restricted to the genitalia in that areolar engorgement also occurs, sometimes to the extent that it masks the antecedent nipple erection that usually accompanies the excitement phase.

The vasodilation and vasocongestive responses described herein may also be induced by pharmacological action without psychological stimulation or arousal by the female. Similarly, the male sexual response may also be induced by pharmacological action without psychological stimulation or arousal.

The present invention is directed to the treatment and/or prevention of sexual dysfunctions in animals, including males and females, by administering the compounds and compositions described herein. The present invention is also directed to improving and/or enhancing the sexual response in animals, including males and females, by administering the compounds and/or compositions described herein. The novel compounds and novel compositions of the present invention are described in more detail below.

The α-adrenergic receptor antagonists that are nitrosated or nitrosylated in accordance with the invention and/or are included in the compositions of the invention can be any of those known in the art, including those exemplified below. Structurally, the α-antagonists can generally be categorized as haloalkylamines, imidazolines, quinozolines, indole derivatives, phenoxypropanolamines, alcohols, alkaloids, amines, piperizines and piperidines.

The first group of α-antagonists are the haloalkylamines that irreversibly block $\alpha_1$- and $\alpha_2$-adrenergic receptors. Included in this group are, for example, phenoxybenzamine and dibenamine. Phenoxybenzamine is used in the treatment of pheochromocytomas, tumors of the adrenal medulla and sympathetic neurons that secrete catecholamines into the circulation. It controls episodes of severe hypertension and minimizes other adverse effects of catecholamines such as contraction of plasma volume and injury of the myocardium.

Another group of α-antagonists are the imidazolines. These include phentolamine and tolazoline. Phentolamine has similar affinity for $\alpha_1$ and $\alpha_2$ receptors. Phentolamine is used in short-term control of hypertension in patients with pheochromocytoma and direct, intracavernous injection of phentolamine (usually in combination with papaverine) has been proposed as a treatment for male sexual dysfunction. Tolazoline is used in the treatment of persistent pulmonary hypertension in neonates. Other imidazolines include, for example, idazoxan, deriglidole, RX 821002, BRL 44408 and BRL 44409 (see, Young et al, *Eur. J. Pharm.*, 168:381–386 (1989), the disclosure of which is incorporated herein by reference).

Another group of α-antagonist compounds that are contemplated are the quinazolines. These include, for example, prazosine, a very potent and selective $\alpha_1$-adrenergic antagonist, terazosin, doxazosin, alfuzosin, bunazosin, ketanserin, trimazosin and abanoquil. This group of compounds is principally used in the treatment of primary systemic hypertension and also in the treatment of congestive heart failure.

Another class of α-adrenergic blocking agents are indoles and indole derivatives. These include, for example, carvedilol and BAM 1303.

Another class of α-adrenergic blocking agents are alcohols. These include, for example, labetelol and ifenprodil.

Another class of α-adrenergic blocking agents are alkaloids. These include, for example, "ergotoxine" which is a mixture of three alkaloids: ergocornine, ergocristine and ergocryptine. Both natural and dihydrogenated peptide alkaloids produce α-adrenergic blockade. The principal uses are to stimulate contraction of the uterus postpartum and to relieve the pain of migraine headaches. Another indole alkaloid is yohimbine. This compound is a competitive antagonist that is selective for $\alpha_2$-adrenergic receptors. In humans, it has been observed to increase blood pressure and heart rate and has been used in the treatment of male sexual dysfunction. Other alkaloid α-blockers include rauwolscine, corynathine, raubascine, tetrahydroalstonine, apoyohimbine, akuammigine, β-yohimbine, yohimbol, pseudoyohimbine and epi-3α-yohimbine.

Another class of α-adrenergic blocking agents are amines. These include, for example, tamsulosin, benoxathian, atipamezole, BE 2254, WB 4101 and HU-723.

Another class of α-adrenergic blocking agents are piperizines, which include, for example, naftopil and saterinone.

Another class of α-adrenergic blocking agents are piperidines. These include, for example, haloperidol.

Each of the above contemplated α-antagonists is described more fully in the literature, such as in Goodman and Gilman, The Pharmacological Basis of Therapeutics (8th Edition), McGraw-Hill (1990), the disclosure of which is incorporated by reference herein in its entirety.

One skilled in the art will understand that the compounds of the present invention which have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. It is intended that the present invention anticipates and includes within its scope all such isomers and mixtures thereof.

One embodiment of the invention includes substituted compounds of the formula I:

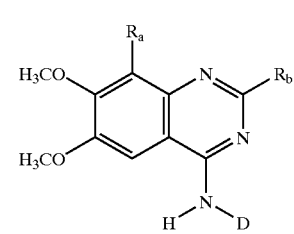

I wherein $R_a$ is a hydrogen or an alkoxy;
$R_b$ is:

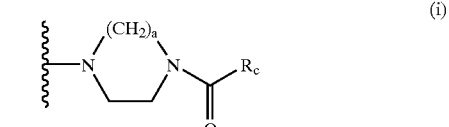

(i)

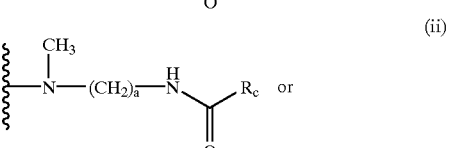

(ii)

or

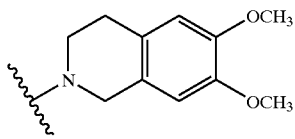
(iii)

wherein a is an integer of 2 or 3;

$R_c$ is a heteroaryl, a heterocyclic ring, a lower alkyl, a hydroxyalkyl, or an arylheterocyclic ring;

D is (i) —NO, (ii) —NO$_2$, (iii) —C(R$_d$)—O—C(O)1—Y—Z—(C(R$_e$)(R$_f$))$_p$—T—Q, wherein R$_d$ is a hydrogen, a lower alkyl, a cycloalkyl, an aryl, an arylalkyl, or a heteroaryl; Y is oxygen, sulfur, carbon or NR$_i$ wherein R$_i$ is a hydrogen or a lower alkyl; R$_e$ and R$_f$ are each independently a hydrogen, a lower alkyl, a haloalkyl, a cycloalkyl, an alkoxy, an aryl, a heteroaryl, an arylalkyl, an amino, an alkylamino, a dialkylamino, an amido, an alkylamido, a carboxylic acid, a carboxylic ester, a carboxamido, a carboxy or —T—Q, or R$_e$ and R$_f$ taken together with the carbon atoms to which they are attached are a carbonyl, a heterocyclic ring, a cycloalkyl or a bridged cycloalkyl; p is an integer from 1 to 10; T is independently a covalent bond, oxygen, sulfur or nitrogen; Z is a covalent bond, a lower alkyl, a haloalkyl, a cycloalkyl, an aryl, a heteroaryl, an arylalkyl, a heteroalkyl, an arylheterocyclic ring or (C(R$_e$)(R$_f$))$_p$, and Q is —NO or —NO$_2$; (iv) —C(O)—Y—Z—(G—(C(R$_e$)(R$_f$))$_q$—T—Q)$_p$, wherein G is a covalent bond, —T—C(O)—, —C(O)—T— or T, wherein q is an integer from 0 to 5, and wherein R$_e$, R$_f$, p, Q, Z, Y and T are as defined above, or (v) —P—Z—(G—(C(R$_e$)(R$_f$))$_q$—T—Q)$_p$, wherein P is a carbonyl, a phosphoryl or a silyl, and wherein R$_e$, R$_f$, p, q, Q, T, Z and G are as defined above.

Another embodiment of the invention includes substituted compounds of the formula II:

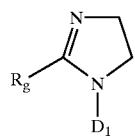
II wherein R$_g$ is:

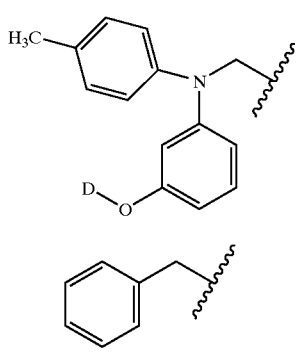
(i)

(ii)

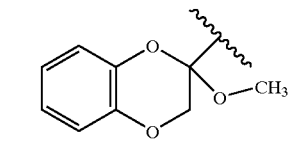
(iii)

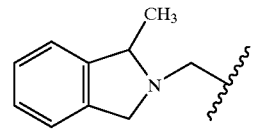
(iv)

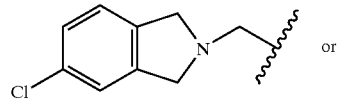
(v) or

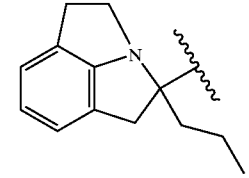
(vi)

wherein D$_1$ is a hydrogen or D, wherein D is as defined above, with the proviso that D$_1$ must be D if there is no other D in the molecule.

Another embodiment of the invention includes substituted compounds of the formula III:

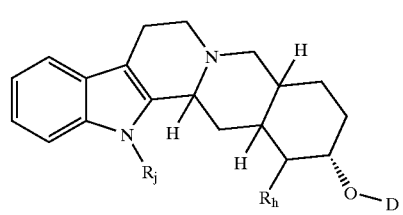
III wherein R$_h$ is a hydrogen, —C(O)—OR$_d$ or —C(O)—X; wherein X is (1) —Y—(C(R$_e$(R$_f$)$_p$—T—Q; wherein G is a covalent bond, —T—C(O)—, —C(O)—T—, or —C(Y—C(O)—R$_m$)—, wherein R$_m$ is a heteroaryl or a heterocyclic ring; and wherein Y, R$_d$, R$_e$, R$_f$, p, Q and T are as defined above; or (2)

wherein W is a heterocyclic ring or NR$_i$R'$_i$; wherein R$_i$ and R'$_i$ are independently a lower alkyl, an aryl or an alkenyl; and wherein R$_j$ is hydrogen, —D or —(O)CR$_d$ wherein D and R$_d$ are as defined above.

Another embodiment of the invention includes substituted compounds of the formula IV:

IV wherein $A_1$ is oxygen or methylene, and X and $R_j$ are as defined above.

Another embodiment of the invention includes substituted compounds of the formula V:

V wherein $R_k$ is a hydrogen or a lower alkyl; and wherein $R_l$ is:

(i)

(ii)

(iii)

(iv)

wherein b is an integer of 0 or 1; D and $D_1$ are as defined above; and $R_n$ is:

(i)

(ii)

(iii)

(iv)

wherein $A_2$ is oxygen or sulfur.

Another embodiment of the invention includes substituted compounds of the formula VI:

VI wherein $R_o$ is:

(i)

(ii)

(iii)

and $R_p$ is:

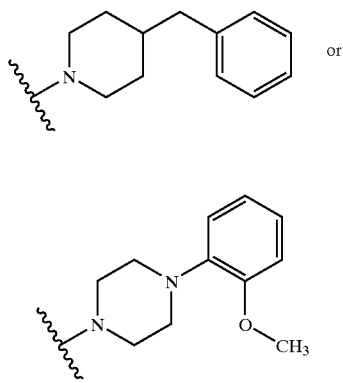

and $R_k$, $D_1$ and D are as defined above.

Another embodiment of the invention includes substituted compounds of the formula VII:

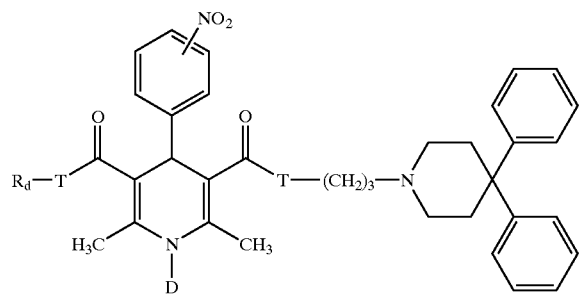

wherein $R_d$, T and D are defined as above.

Another embodiment of the invention includes substituted compounds of the formula VIII:

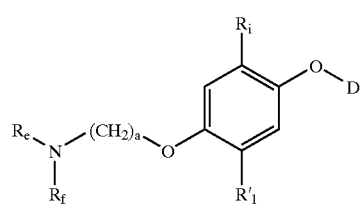

wherein a, $R_i$, $R'_i$, $R_e$, $R_f$ and D are as defined above.

The present invention also relates to processes for preparing the compounds of formula (I), (II), (III), (IV), (V), (VI), (VII) and (VIII) and to the intermediates useful in such processes.

Some of the nitrosated and nitrosylated α-antagonists of the present invention may be synthesized as shown in reaction Schemes I through XXI presented below, wherein $R_a$, $R_b$, $R_c$, $R_d$, $R_e$, $R_f$, $R_g$, $R_h$, $R_i$, $R'_i$, $R_j$, $R_k$, $R_l$, $R_m$, $R_n$, $R_o$, $R_p$, $A_1$, $A_2$, a, n, W and X are as defined above or as depicted in the reaction schemes for formulas I, II, III, IV, V, VI, VII or VIII. $P^1$ is an oxygen protecting group and $P^2$ is a sulfur protecting group. The reactions are performed in solvents appropriate to the reagents and materials used are suitable for the transformations being effected. It is understood by one skilled in the art of organic synthesis that the functionality present in the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to one skilled in the art. The use of sulfur and oxygen protecting groups is well known in the art for protecting thiol and alcohol groups against undesirable reactions during a synthetic procedure and many such protecting groups are known, such as those described by T. H. Greene and P. G. M. Wuts, *Protective Groups in Organic Synthesis*, John Wiley & Sons, New York (1991), the disclosure of which is incorporated by reference herein in its entirety.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by one skilled in the art. In all such cases, either the reactions can be successfully performed by conventional modifications known to one skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Nitroso compounds of formula (I) wherein $R_a$, $R_b$, $R_e$, $R_f$, and p are as defined above and an O-nitrosylated amide is representative of the D group as defined above may be prepared according to Scheme I. The amine group of the quinazoline of the formula 1 is converted to the amide of the formula 2 wherein p, $R_e$ and $R_f$ are as defined above by reaction with an appropriate protected alcohol containing activated acylating agent wherein $P^1$ is as defined above. Preferred methods for the formation of amides are reacting the amine with the preformed acid chloride or symmetrical anhydride of the protected alcohol-containing acid. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction with a suitable nitrosylating agent such as thionyl chloride nitrite, thionyl dinitrite, or nitrosium tetrafluoroborate in a suitable anhydrous solvent such as dichloromethane, THF, DMF, or acetonitrile with or without an amine base such as pyridine or triethylamine affords the compound of the formula IA.

Scheme I

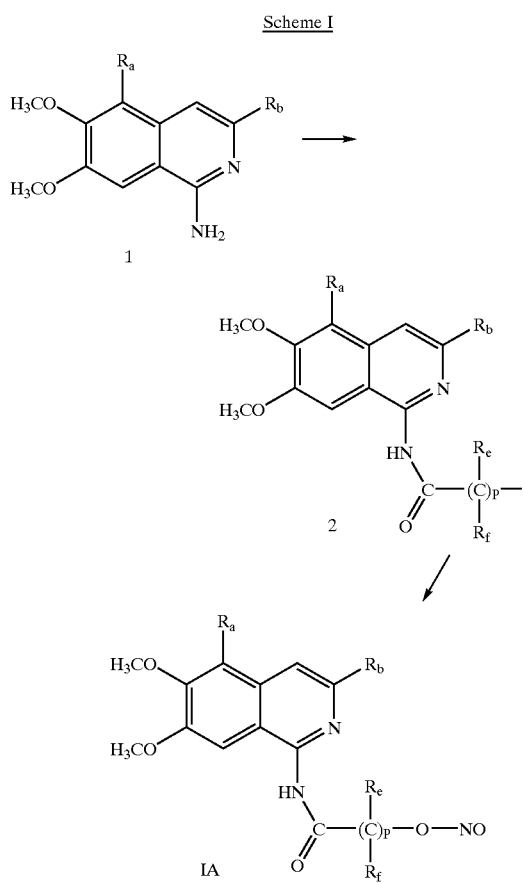

Nitroso compounds of formula (I) wherein $R_a$, $R_b$, $R_e$, $R_f$, and p are as defined above and an S-nitrosylated amide is representative of the D group as defined above may be prepared according to Scheme II. The amine group of the quinazoline of the formula 1 is converted to the amide of the formula 3, wherein p, $R_e$ and $R_f$ are defined as above by reaction with an appropriate protected thiol-containing activated acylating agent wherein $P^2$ is as defined above. Preferred methods for the formation of amides are reacting the amine with the preformed acid chloride or symmetrical anhydride of the protected thiol containing acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a S-triphenylmethyl thioether. Deprotection of the thiol moiety (zinc in dilute aqueous acid, triphenyl-phosphine in water and sodium borohydride are preferred methods for reducing disulfide groups while an aqueous base is typically utilized to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group) followed by reaction with a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methylene chloride, THF, DMF, or acetonitrile with or without an amine base such as pyridine or triethylamine affords the compound of the formula IB. Alternatively, treatment of compound 3 with a stoichiometric quantity of sodium nitrite in aqueous acid affords the compound of the formula IB.

Scheme II

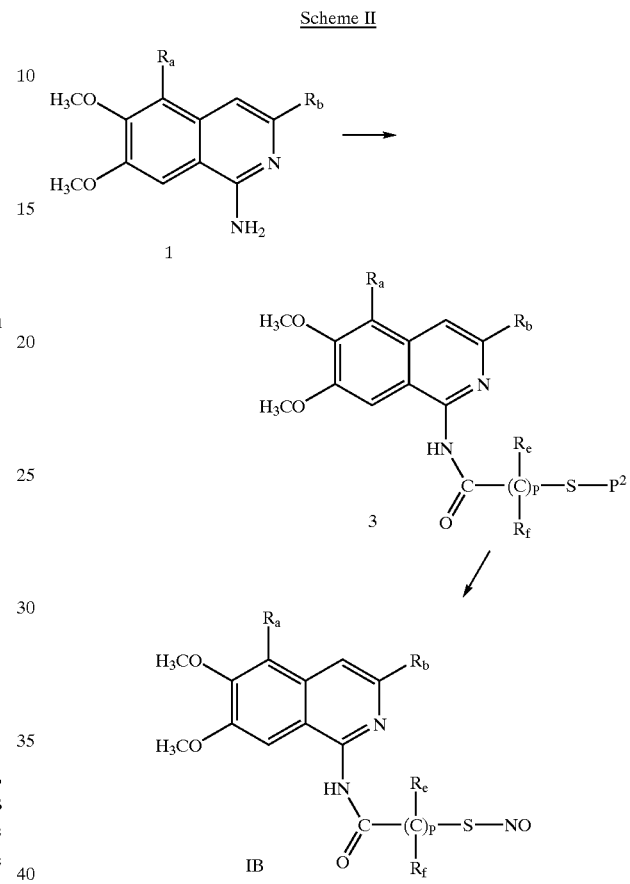

Nitro compounds of formula (I) wherein $R_a$, $R_b$, $R_e$ $R_f$, and p are defined as above and an O-nitrosated amide is representative of the D group as defined above may be prepared according to Scheme III. The amine group of the quinazoline of the formula 1 is converted to the amide of the formula IC wherein p, $R_e$ and $R_f$ are defined as above by reaction with an appropriate nitrate containing activated acylating agent. Preferred methods for the formation of amides are reacting the amine with the preformed acid chloride or symmetrical anhydride of the nitrate containing acid to afford the compound of the formula IC.

Scheme III

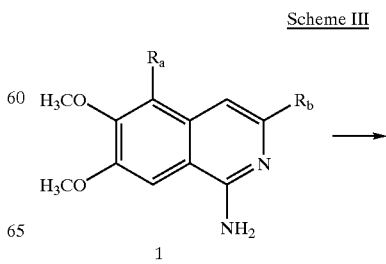

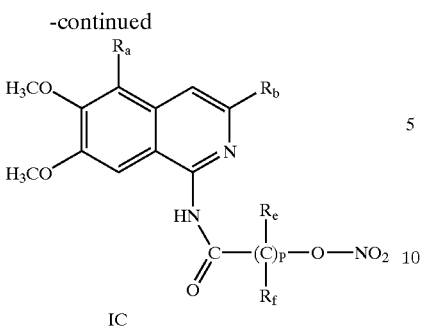

IC

Nitroso compounds of formula (II) wherein $R_e$, $R_f$, $R_g$, and p are as defined above and an O-nitrosylated acyl imidazoline is representative of the D group as defined above may be prepared according to Scheme IV. The imidazoline group of the formula 4 is converted to the acyl imidazoline of the formula 5 wherein p, $R_e$ and $R_f$ are defined as above by reaction with an appropriate protected alcohol containing activated acylating agent wherein $P^1$ is as defined above. Preferred methods for the formation of acyl imidazolines are reacting the imidazoline with the preformed acid chloride or symmetrical anhydride of the protected alcohol containing acid. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction with a suitable nitrosylating agent such as thionyl chloride nitrite, thionyl dinitrite, or nitrosium tetrafluoroborate in a suitable anhydrous solvent such as dichloromethane, THF, DMF, or acetonitrile with or without an amine base such as pyridine or triethylamine affords the compound of the formula IIA.

Scheme IV

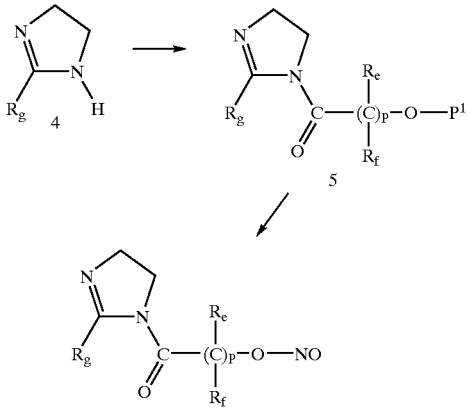

Nitroso compounds of formula (II) wherein $R_e$, $R_f$, $R_g$, and p are defined as above and an S-nitrosylated acyl imidazoline is representative of the D group as defined above may be prepared according to Scheme V. The imidazoline group of the formula 4 is converted to the acyl imidazoline of the formula 6 wherein p, $R_e$ and $R_f$ are defined as above by reaction with an appropriate protected alcohol containing activated acylating agent wherein $P^2$ is as defined above. Preferred methods for the formation of acyl imidazolines are reacting the imidazoline with the preformed acid chloride or symmetrical anhydride of the protected thiol containing acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a S-triphenylmethyl thioether. Deprotection of the thiol moiety (zinc in dilute aqueous acid, triphenylphosphine in water and sodium borohydride are preferred methods for reducing disulfide groups while aqueous base is typically used to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group) followed by reaction with a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methylene chloride, THF, DMF or acetonitrile with or without an amine base such as pyridine or triethylamine affords the compound of the formula IIB. Alternatively, treatment of compound 6 with a stoichiometric quantity of sodium nitrite in aqueous acid affords the compound of the formula IIB.

Scheme V

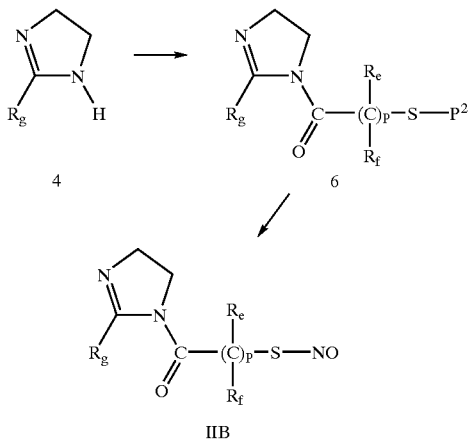

IIB

Nitro compounds of formula (II) wherein $R_e$, $R_f$, $R_g$, and p are defined as above and an O-nitrosated acyl imidazoline is representative of the D group as defined above may be prepared according to Scheme VI. The imidazoline group of the formula 4 is converted to the acyl imidazoline of the formula IIC wherein p, $R_e$ and $R_f$ are defined as above by reaction with an appropriate nitrate containing activated acylating agent. Preferred methods for the formation of acyl imidazolines are reacting the amine with the preformed acid chloride or symmetrical anhydride of the nitrate containing acid to afford the compound of the formula IC.

Scheme VI

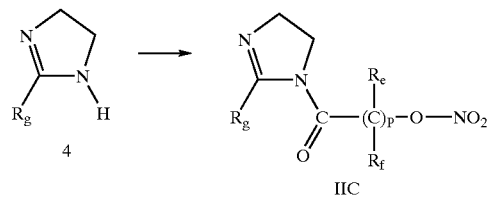

IIC

Nitroso compounds of formula (III) wherein $R_e$, $R_f$, $R_h$, $R_j$, and p are defined as above and an O-nitrosylated ester is representative of the D group as defined above may be prepared according to Scheme VII. The alcohol group of formula 7 is converted to the ester of formula 8 wherein p, $R_e$ and $R_f$ are defined as above by reaction with an appropriate protected alcohol containing activated acylating agent wherein $P^1$ is as defined above. Preferred methods for the formation of esters are reacting the alcohol with the preformed acid chloride or symmetrical anhydride of the protected alcohol containing acid. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction with a suitable nitrosylating agent such as thionyl chloride nitrite, thionyl dinitrite, or nitrosium tetrafluoroborate in a suitable anhydrous solvent such as dichloromethane, THF, DMF, or acetonitrile with or without an amine base such as pyridine or triethylamine affords the compound of the formula IIIA.

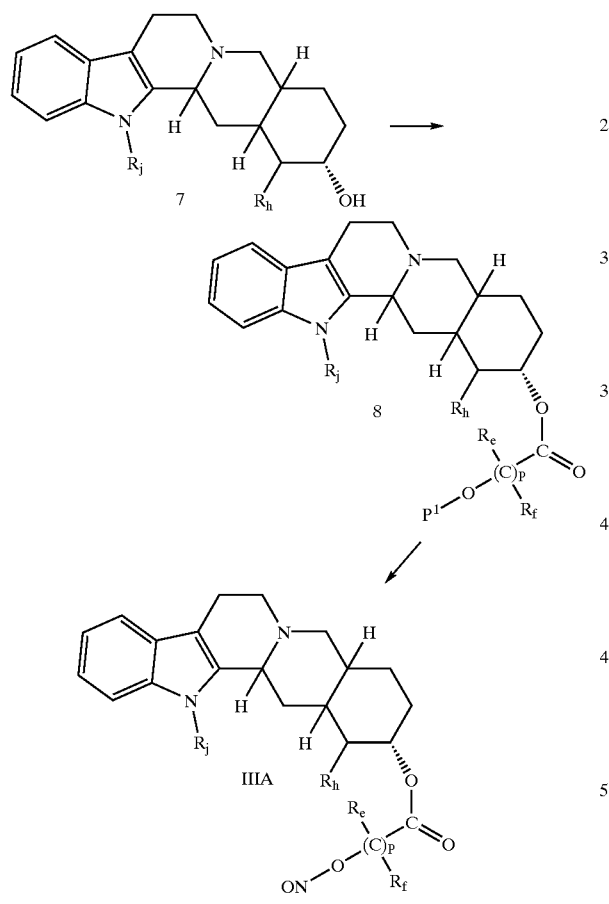

Scheme VII

Nitroso compounds of formula (III) wherein $R_e$, $R_f$, $R_h$, $R_j$, and p are defined as above and an S-nitrosylated ester is representative of the D group as defined above may be prepared according to Scheme III. The alcohol group of the formula 7 is converted to the ester of the formula 9 wherein p, $R_e$ and $R_f$ are defined as above by reaction with an appropriate protected thiol containing activated acylating agent wherein $P^2$ is as defined above. Preferred methods for the formation of esters are reacting the alcohol with the preformed acid chloride or symmetrical anhydride of the protected thiol containing acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a S-triphenylmethyl thioether. Deprotection of the thiol moiety (zinc in dilute aqueous acid, triphenylphosphine in water and sodium borohydride are preferred methods for reducing disulfide groups while an aqueous base is typically used to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group) followed by reaction a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methylene chloride, THF, DMF, or acetonitrile with or without an amine base such as pyridine or triethylamine affords the compound of the formula IIIB. Alternatively, treatment of compound 9 with a stoichiometric quantity of sodium nitrite in aqueous acid affords the compound of the formula IIIB.

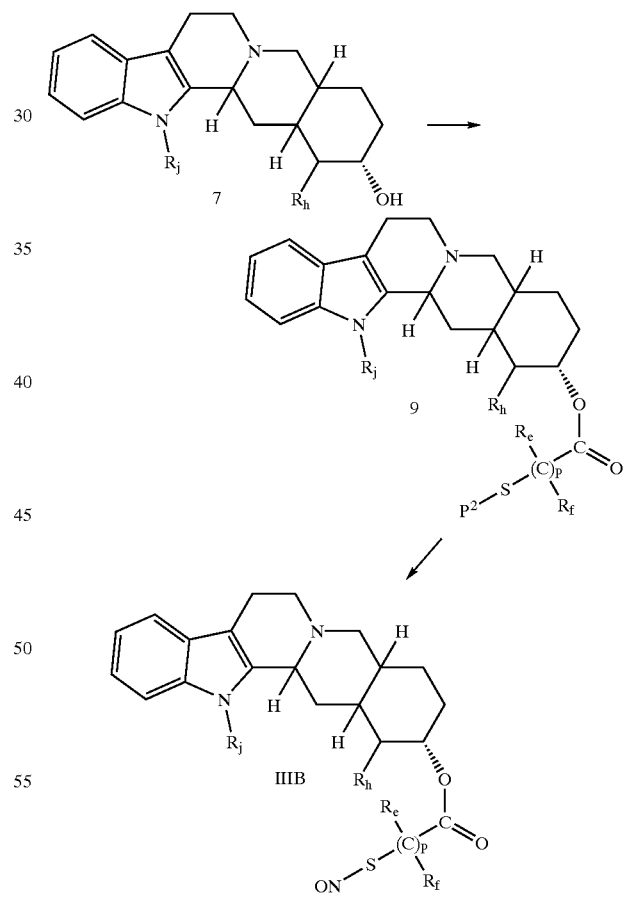

Scheme VIII

Nitro compounds of formula (III) wherein $R_e$, $R_f$, $R_h$, $R_j$, and p are defined as above and an O-nitrosated ester is representative of the D group as defined above may be prepared according to Scheme IX. The alcohol group of the formula 7 is converted to the ester of the formula IIIC wherein p, $R_e$ and $R_f$ are defined as above by reaction with an appropriate nitrate containing activated acylating agent. Preferred methods for the formation of esters are reacting the alcohol with the preformed acid chloride or symmetrical anhydride of the nitrate containing acid to afford a compound of the formula IIIC.

Scheme IX

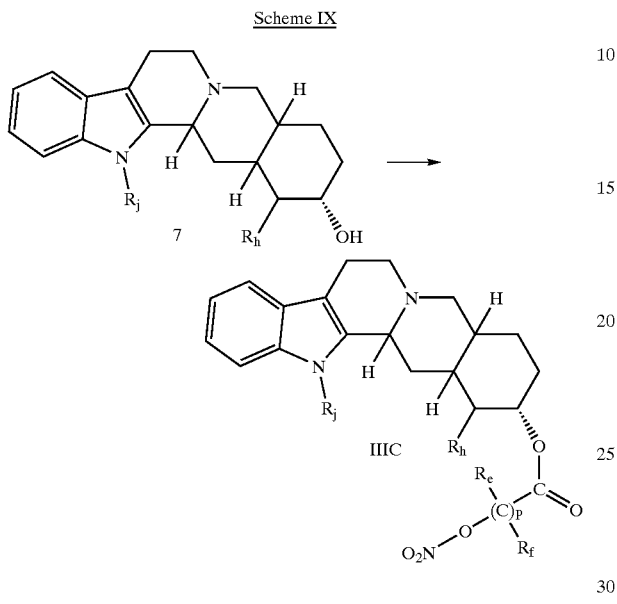

Nitroso compounds of formula (IV) wherein $A_1$, $R_e$, $R_f$, $R_h$, $R_j$, and p are defined as above and an O-nitrosylated ester is representative of the X group as defined above may be prepared according to Scheme X. An acid of the formula 10 is converted into the ester of the formula 11 wherein p, $R_e$, and $R_f$ are defined as above by reaction with an appropriate monoprotected diol. Preferred methods for the preparation of esters are initially forming the mixed anhydride via reaction of 10 with a chloroformate such as isobutylchloroformate in the presence of a non nucleophilic base such as triethylamine in an anhydrous inert solvent such as dichloromethane, diethylether, or THF. The mixed anhydride is then reacted with the monoprotected alcohol preferably in the presence of a condensation catalyst such as 4-dimethylamino pyridine. Alternatively, the acid 10 may be first converted to the acid chloride by treatment with oxalyl chloride in the presence of a catalytic amount of DMF. The acid chloride is then reacted with the monoprotected alcohol preferably in the presence of a condensation catalyst such as 4-dimethylaminopyridine and a tertiary amine base such as triethyl amine to afford the ester 11. Alternatively, the acid 10 and monoprotected diol may be coupled to afford 11 by treatment with a dehydration agent such as dicyclohexylcarbodiimide. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction with a suitable nitrosylating agent such as thionyl chloride nitrite, thionyl dinitrite, or nitrosium tetrafluoroborate in a suitable anhydrous solvent such as dichloromethane, THF, DMF, or acetonitrile affords the compound of the formula IVA.

Scheme X

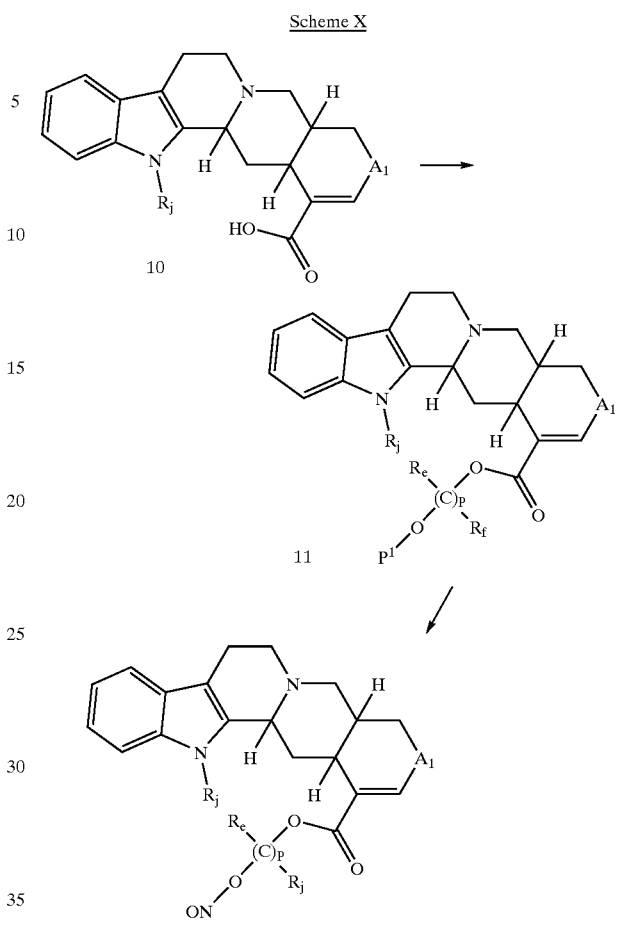

Nitroso compounds of formula (IV) wherein $A_1$, $R_f$, $R_h$, $R_j$, and p are defined as above and an S-nitrosylated ester is representative of the X group as defined above may be prepared according to Scheme XI. An acid of the formula 10 is converted into the ester of the formula 12 wherein p, $R_e$, and $R_f$ are defined as above and a S-nitrosylated ester is representative of the X group as defined above by reaction with an appropriate protected thiol containing alcohol. Preferred methods for the preparation of esters are initially forming the mixed anhydride via reaction of 10 with a chloroformate such as isobutylchloroformate in the presence of a non nucleophilic base such as triethylamine in an anhydrous inert solvent such as diethylether or THF. The mixed anhydride is then reacted with the thiol containing alcohol preferably in the presence of a condensation catalyst such as 4-dimethylaminopyridine. Alternatively, the acid 10 may be first converted to the acid chloride be treatment with oxalyl chloride in the presence of a catalytic amount of DMF. The acid chloride is then reacted with the monoprotected thiol preferably in the presence of a condensation catalyst such as 4-dimethylaminopyridine and a tertiary amine base such as triethyl amine to afford the ester 12. Alternatively, the acid and thiol containing alcohol may be coupled to afford 12 by treatment with a dehydration agent such as dicyclohexylcarbodiimide. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether, or a S-triphenylmethyl thioether. Deprotection of the thiol moiety (zinc in dilute aqueous acid, triphenylphosphine in water and sodium borohydride are preferred methods for reducing disulfide groups while aqueous base is typically used to hydrolyze thiolesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group) followed by reaction with a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methylene chloride, THF, DMF or acetonitrile with or without an amine base such as pyridine or triethylamine affords the compound of the formula IVB. Alternatively, treatment of compound 12 with a stoichiometric quantity of sodium nitrite in aqueous acid affords the compound of the formula IVB.

Scheme XI

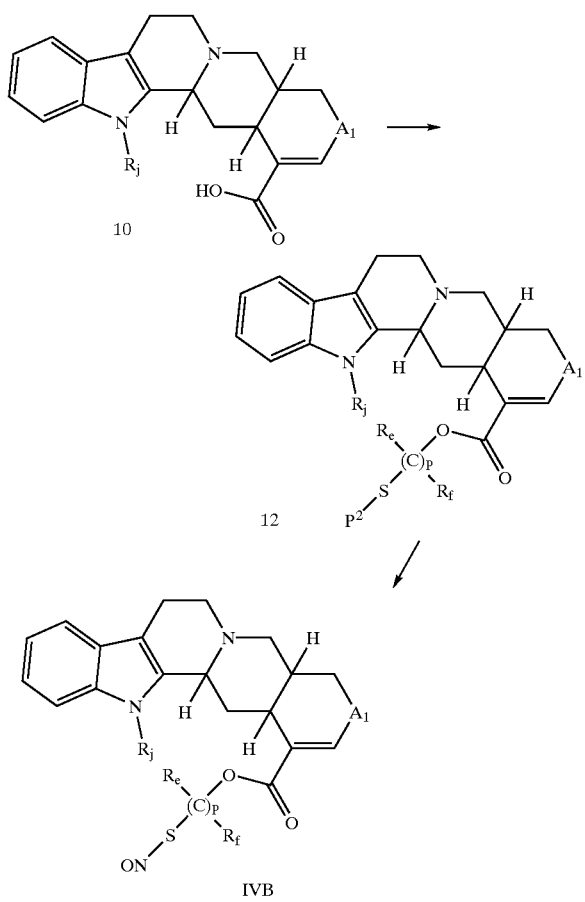

Nitro compounds of formula (IV) wherein $A_1$, $R_e$, $R_f$, $R_h$, $R_j$, and p are defined as above and an O-nitrosated ester is representative of the X group as defined above may be prepared according to Scheme XII. An acid of the formula 10 is converted into the ester of the formula IVC wherein p, $R_e$, and $R_f$ are defined as above by reaction with an appropriate nitrate containing alcohol. Preferred methods for the preparation of esters are initially forming the mixed anhydride via reaction of 10 with a chloroformate such as isobutylchloroformate in the presence of a non nucleophilic base such as triethylamine in an anhydrous inert solvent such as dichloromethane, diethylether, or THF. The mixed anhydride is then reacted with the nitrate containing alcohol preferably in the presence of a condensation catalyst such as 4-dimethylamino-pyridine. Alternatively, the acid 10 may be first converted to the acid chloride by treatment with oxalyl chloride in the presence of a catalytic amount of DMF. The acid chloride is then reacted with the nitrate containing alcohol preferably in the presence of a condensation catalyst such as 4-dimethylaminopyridine and a tertiary amine base such as triethyl amine to afford the a compound of the formula IVC. Alternatively, the acid 10 and nitrate containing alcohol may be coupled to afford a compound of the formula IVC by treatment with a dehydration agent such as dicyclohexylcarbodiimide.

Scheme XII

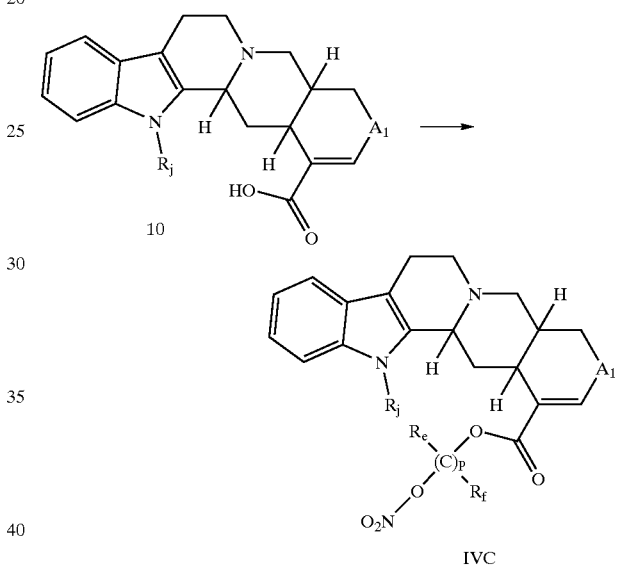

Nitroso compounds of formula (V) wherein $R_e$, $R_f$, $R_k$, $R_l$, $R_n$, and p are defined as above and an O-nitrosylated N-acyloxyalkyl amine is representative of the D group as defined above may be prepared according to Scheme XIII. The amine group of the compound of the formula 13 is converted to the N-acyloxyalkyl amine of the formula 14 wherein p, $R_e$, and $R_f$ are defined as above by reaction with an appropriate protected alcohol containing chloromethyl acyl derivative wherein $P^1$ is as defined above. Preferred methods for the formation of N-acyloxyalkyl amines are reacting the amine with the preformed chloromethyl acyloxyalkyl derivative of the protected alcohol. Preferred protecting groups for the alcohol moiety are silyl ethers such as a triethylsilyl or a tert-butyldimethylsilyl ether. Deprotection of the hydroxyl moiety (fluoride ion is the preferred method for removing silyl ether protecting groups) followed by reaction with a suitable nitrosylating agent such as thionyl chloride nitrite, thionyl dinitrite, or nitrosium tetrafluoroborate in a suitable anhydrous solvent such as dichloromethane, THF, DMF, or acetonitrile with or without an amine base such as pyridine or triethylamine affords the compound of the formula VA.

Scheme XIII

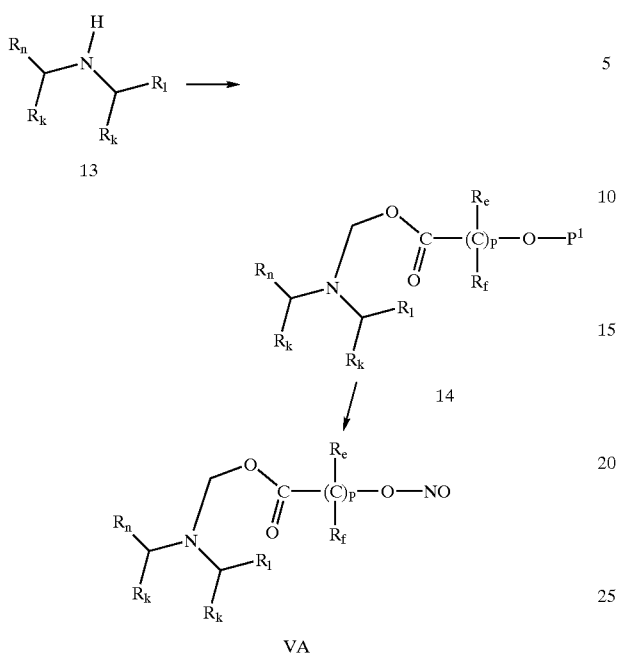

VA

Nitroso compounds of formula (V) wherein $R_e$, $R_f$, $R_k$, $R_l$, $R_n$, and p are defined as above and an S-nitrosylated N-acyloxyalkyl amine is representative of the D group as defined above may be prepared according to Scheme XIV. The amine group of the compound of the formula 13 is converted to the N-acyloxyalkyl amine of the formula 15 wherein p, $R_e$ and $R_f$ are defined as above by reaction with an appropriate protected thiol containing chloromethyl acyl derivative wherein $P^2$ is as defined above. Preferred protecting groups for the thiol moiety are as a thioester such as a thioacetate or thiobenzoate, as a disulfide, as a thiocarbamate such as N-methoxymethyl thiocarbamate, or as a thioether such as a tetrahydropyranyl thioether. Deprotection of the thiol moiety (triphenylphosphine in water and sodium borohydride are preferred methods for reducing disulfide groups while an aqueous base is typically used to hydrolyze thioesters and N-methoxymethyl thiocarbamates and mercuric trifluoroacetate or silver nitrate are used to remove a tetrahydropyranyl thioether group) followed by reaction with a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methylene chloride, THF, DMF, or acetonitrile with or without an amine base such as pyridine or triethylamine affords the compound of the formula VB.

Scheme XIV

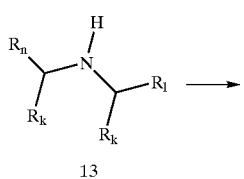

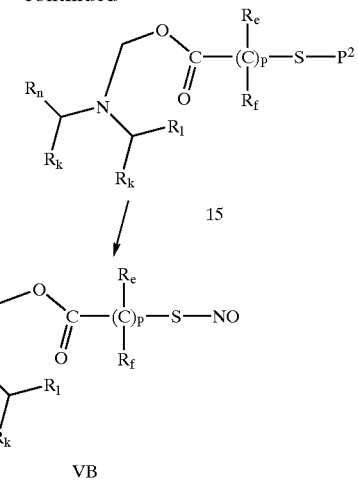

VB

Nitro compounds of formula (V) wherein $R_e$, $R_f$, $R_k$, $R_l$, $R_n$, and p are defined as above and an O-nitrosated N-acyloxyalkyl amine is representative of the D group as defined above may be prepared according to Scheme XV. The amine group of the compound of the formula 13 is converted to the N-acyloxyalkyl amine of the formula VC wherein p, $R_e$ and $R_f$ are defined as above by reaction with an appropriate nitrate containing chloromethyl acyl derivative. Preferred methods for the formation of N-acyloxyalkyl amines are reacting the amine with the preformed chloromethyl acyloxyalkyl derivative of the nitrate containing derivative to afford the compound of the formula VC.

Scheme XV

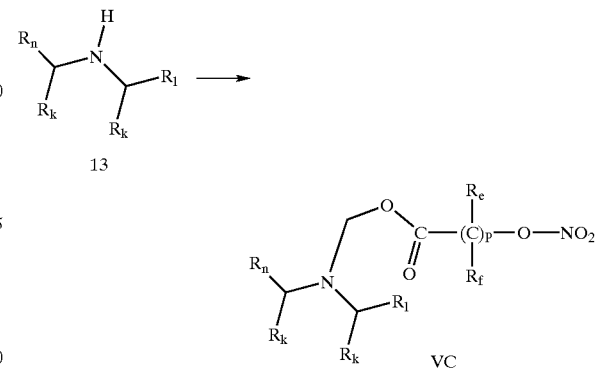

Nitroso compounds of formula (VII) wherein $R_d$, $R_e$, $R_f$, T, and p are defined as above and an O-nitrosylated amide is representative of the D group as defined above may be prepared according to Scheme XVI. The amine group of the dihydropyridine of the formula 14 is converted to the amide of the formula 15 wherein p, $R_e$ and $R_f$ are defined as above by reaction with an appropriate protected alcohol containing activated acylating agent wherein $P^1$ is as defined above. Preferred methods for the formation of amides are reacting the amine with the preformed acid chloride or symmetrical anhydride of the protected alcohol containing acid. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction with a suitable nitrosylating agent such as thionyl chloride nitrite, thionyl dinitrite, or nitrosium tetrafluoroborate in a suitable anhydrous solvent such as dichloromethane, THF, DMF, or acetonitrile with or without an amine base such as pyridine or triethylamine affords the compound of the formula VIIA.

Scheme XVI

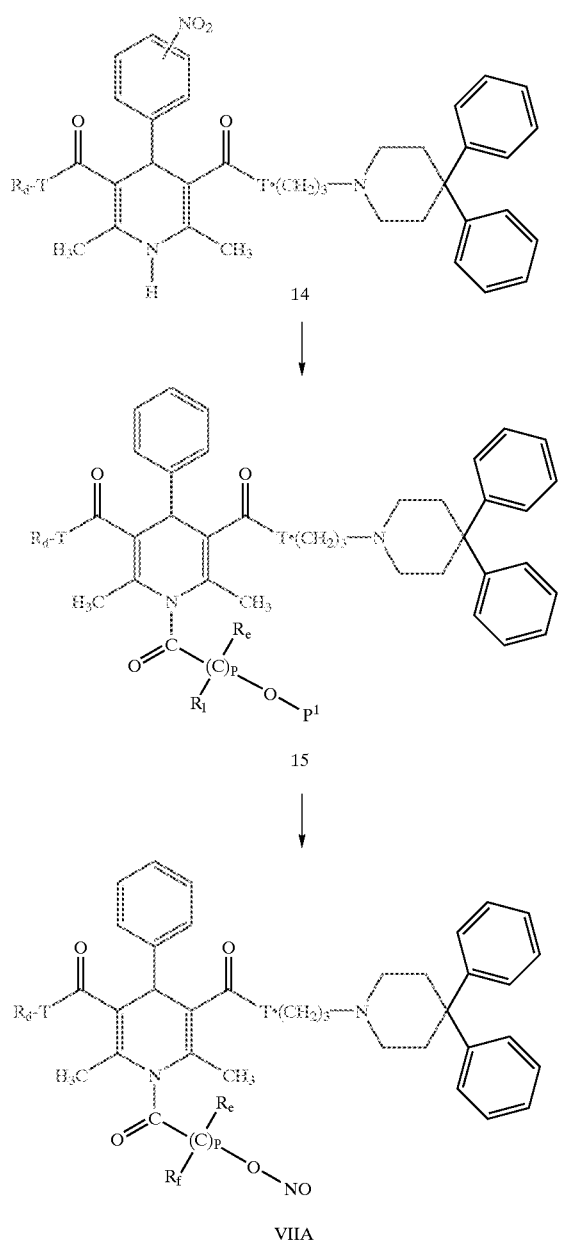

Nitroso compounds of formula (VII) wherein $R_d$, $R_e$, $R_f$, T, and p are defined as above and an S-nitrosylated amide is representative of the D group as defined above may be prepared according to Scheme XVII. The amine group of the dihydropyridine of the formula 14 is converted to the amide of the formula 16 wherein p, $R_e$, and $R_f$ are defined as above by reaction with an appropriate protected thiol containing activated acylating agent wherein $P^2$ is defined above. Preferred methods for the formation of amides are reacting the amine with the preformed acid chloride or symmetrical anhydride of the protected thiol containing acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a S-triphenylmethyl thioether. Deprotection of the thiol moiety (zinc in dilute aqueous acid, triphenylphosphine in water and sodium borohydride are preferred methods for reducing disulfide groups while aqueous base is typically used to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group) followed by reaction with a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methylene chloride, THF, DMF, or acetonitrile with or without an amine base such as pyridine or triethylamine affords the compound of the formula VIIB. Alternatively, treatment of compound 16 with a stoichiometric quantity of sodium nitrite in aqueous acid affords the compound of the formula VIIB.

Scheme XVII

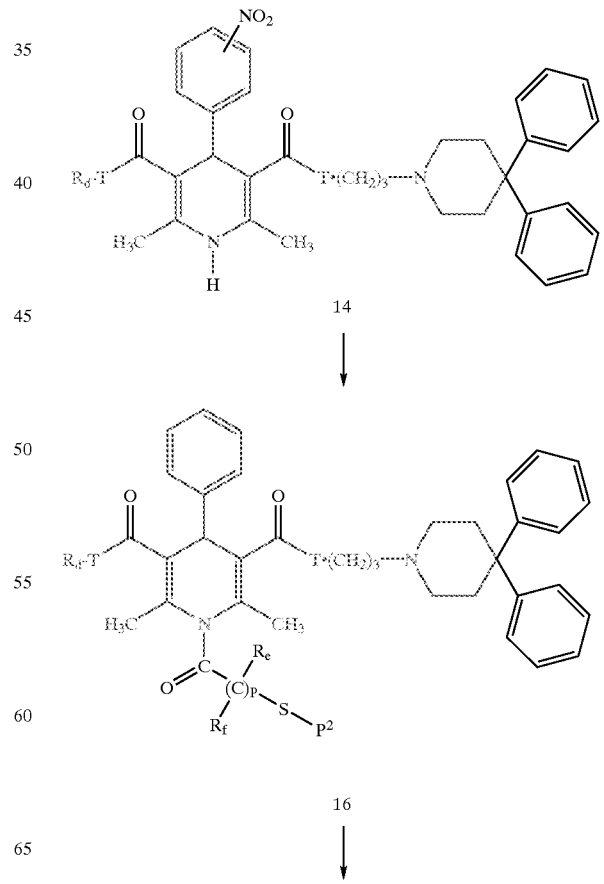

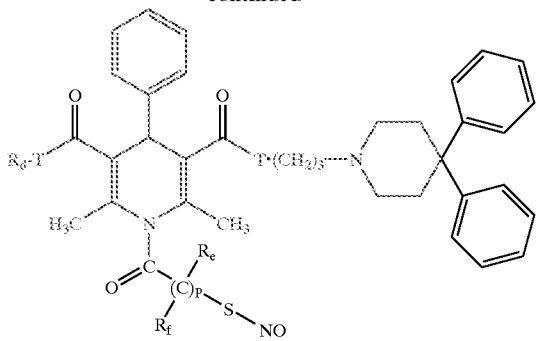

VIIB

Nitro compounds of formula (VII) wherein $R_d$, $R_e$, $R_f$, T, and p are defined as above and an O-nitrosated amide is representative of the D group as defined above may be prepared according to Scheme XVIII. The amine group of the dihydropyridine of the formula 14 is converted to the amide of the formula VIIC wherein p, $R_e$ and $R_f$ are defined as above by reaction with an appropriate nitrate containing activated acylating agent. Preferred methods for the formation of amides are reacting the amine with the preformed acid chloride or symmetrical anhydride of the nitrate containing acid to afford the compound of the formula VIIC.

Scheme XVIII

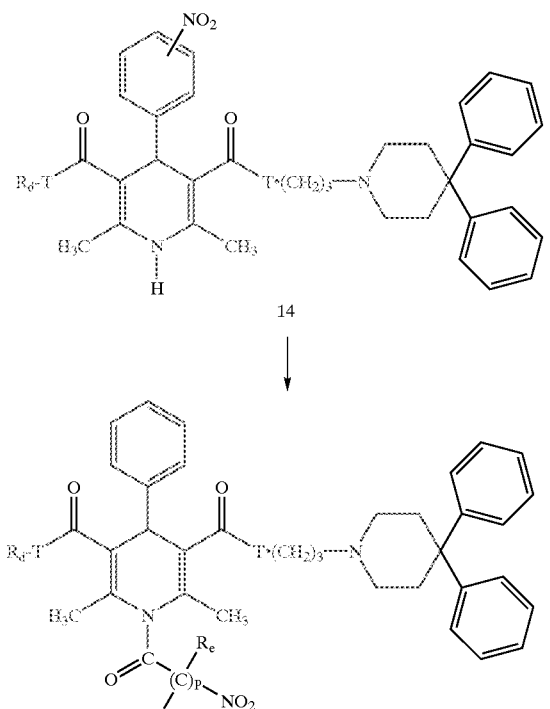

VIIC

Nitroso compounds of formula (VIII) wherein $R_e$, $R_f$, a and p are as defined as above and an O-nitrosylated ester is representative of the D group as defined above may be prepared according to Scheme XIX. The hydroxyl group of the phenol of the formula 15 is converted to the ester of the formula 16 wherein a, p, $R_e$ and $R_f$ are defined as above by reaction with an appropriate protected alcohol containing activated acylating agent wherein $P^1$ is as defined above. Preferred methods for the formation of esters are reacting the hydroxyl with the preformed acid chloride or symmetrical anhydride of the protected alcohol containing acid. Preferred protecting groups for the alcohol moiety are silyl ethers such as a trimethylsilyl or a tert-butyldimethylsilyl ether. Deprotection of the hydroxyl moiety (fluoride ion is the preferred method for removing silyl ether protecting groups) followed by reaction with a suitable nitrosylating agent such as thionyl chloride nitrite, thionyl dinitrite, or nitrosium tetrafluoroborate in a suitable anhydrous solvent such as dichloromethane, THF, DMF or acetonitrile with or without an amine base such as pyridine or triethylamine affords the compound of the formula VIIIA.

Scheme XIX

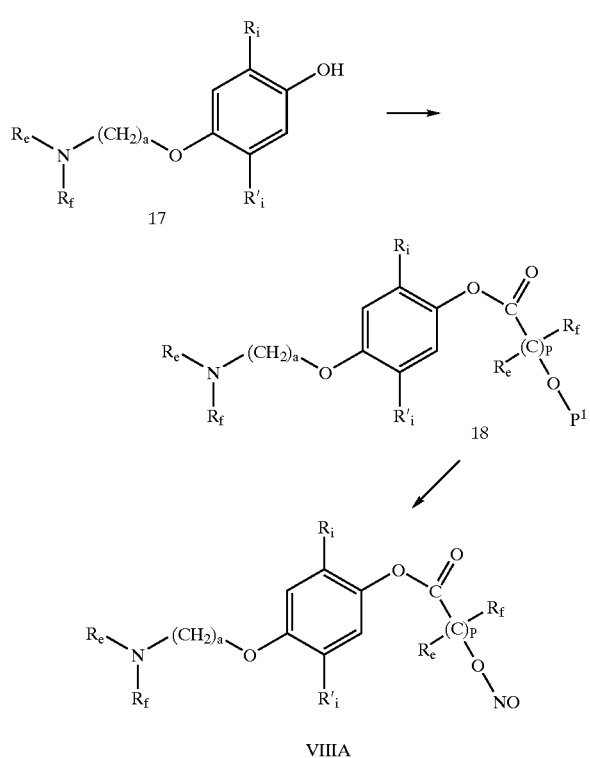

VIIIA

Nitroso compounds of formula (VIII) wherein $R_e$, $R_f$, $R_i$, $R'_i$, a and p are as defined above and an S-nitrosylated ester is representative of the D group as defined above may be prepared according to Scheme XX. The hydroxyl group of the phenol of the formula 17 is converted to the ester of the formula 19 wherein a, p, $R_e$ and $R_f$ are defined as above by reaction with an appropriate protected thiol containing activated acylating agent wherein $P^2$ is as defined above. Preferred methods for the formation of esters are reacting the hydroxyl with the preformed acid chloride or symmetrical anhydride of the protected thiol containing acid. Preferred protecting groups for the thiol moiety are as a thioester such as a thioacetate or thiobenzoate, as a disulfide, as a thiocarbamate such as N-methoxymethyl thiocarbamate, or as a thioether such as a paramethoxybenzyl thioether, a tetrahydropyranyl thioether or a S-triphenylmethyl thioether. Deprotection of the thiol moiety (zinc in dilute aqueous acid, triphenyl-phosphine in water and sodium borohydride are preferred methods for reducing disulfide groups while aqueous base is typically used to hydrolyze thioesters and N-methoxymethyl thiocarbamates and mercuric trifluoroacetate, silver nitrate, or strong acids such as trifluoroacetic or hydrochloric acid and heat are used to remove a paramethoxybenzyl thioether, a tetrahydropyranyl thioether or a S-triphenylmethyl thioether group) followed by reaction with a suitable nitrosylating agent such as thionyl chloride nitrite, thionyl dinitrite, a lower alkyl nitrite such as tert-butyl nitrite, or nitrosium tetrafluoroborate in a suitable anhydrous solvent such as methylene chloride, THF, DMF or acetonitrile with or without an amine base such as pyridine or triethylamine affords the compound of the formula VIIIB. Alternatively, treatment of compound 17 with a stoichiometric quantity of sodium nitrite in aqueous acid affords the compound of the formula VIIIB.

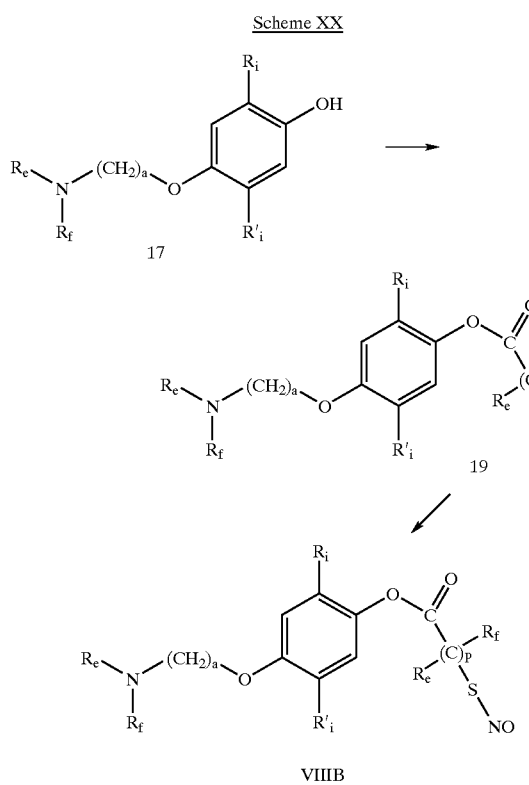

Nitro compounds of formula (VIII) wherein $R_e$, $R_f$, $R_i$, $R'_i$, a and p are as defined above an O-nitrosated ester is representative of the D group as defined above may be prepared according to Scheme XXI. The hydroxyl group of the phenol of the formula 15 is converted to the ester of the formula VIIIC wherein a, p, $R_e$ and $R_f$ are as defined above by reaction with an appropriate nitrate containing activated acylating agent. Preferred methods for the formation of amides are reacting the amine with the preformed acid chloride or symmetrical anhydride of the nitrate containing acid to afford the compound of the formula VIIIC.

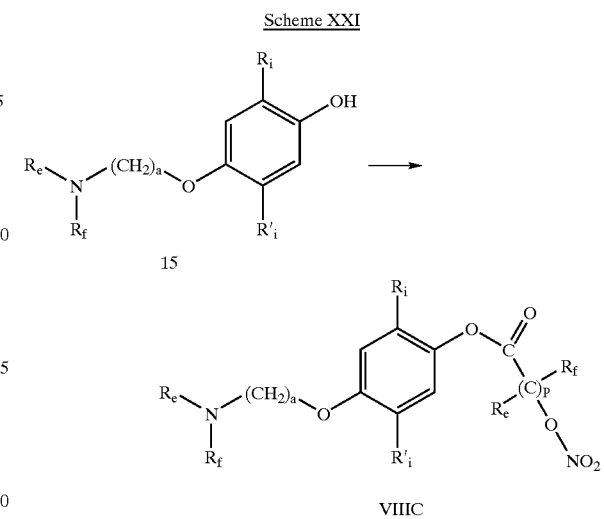

As discussed above, another aspect of the invention provides a composition comprising a therapeutically effective amount of an α-adrenergic receptor antagonist (α-antagonist), which can optionally be substituted with at least one NO or $NO_2$ moiety, and a compound that donates, transfers or releases nitric oxide as a charged species, i.e., nitrosonium ($NO^+$) or nitroxyl ($NO^-$), or as the neutral species, nitric oxide (NO.).

Another embodiment of this aspect is one where the α-blocker is not substituted with at least one NO or $NO_2$ moiety. Additional α-blockers that are suitable for this embodiment include amines, such as tedisamil, mirtazipine, setiptiline, reboxitine and delequamine; amides, such as indoramin and SB 216469; piperizines, such as SL 89.0591, ARC 239, urapidil, 5-methylurapidil and monatepil. Indoramin is a selective, competitive $\alpha_1$-antagonist that has been used for the treatment of hypertension. Urapidil is also known to be a selective $\alpha_1$-adrenergic antagonist that has a hypotensive effect in humans.

The compounds that donate, transfer or release nitric oxide or that elevate levels of endogenous EDRF can be any of those known in the art, including those mentioned and/or exemplified below.

Nitrogen monoxide can exist in three forms: $NO^-$ (nitroxyl), NO. (nitric oxide) and $NO^+$ (nitrosonium). NO. is a highly reactive short-lived species that is potentially toxic to cells. This is critical because the pharmacological efficacy of NO depends upon the form in which it is delivered. In contrast to NO., nitrosonium and nitroxyl do not react with $O_2$ or $O_2^-$ species, and are also resistant to decomposition in the presence of redox metals. Consequently, administration of NO equivalents does not result in the generation of toxic by-products or the elimination of the active NO moiety.

Compounds contemplated for use in the invention are nitric oxide and compounds that release nitric oxide or otherwise directly or indirectly deliver or transfer nitric oxide to a site of its activity, such as on a cell membrane, in vivo. As used herein, the term "nitric oxide" encompasses uncharged nitric oxide (NO•) and charged nitric oxide species, particularly including nitrosonium ion ($NO^+$) and nitroxyl ion ($NO^-$). The reactive form of nitric oxide can be provided by gaseous nitric oxide. The nitric oxide releasing, delivering or transferring compounds, having the structure F—NO wherein F is a nitric oxide releasing, delivering or transferring moiety, include any and all such compounds which provide nitric oxide to its intended site of action in a form active for their intended purpose. As used herein, the term "NO adducts" encompasses any of such nitric oxide releasing, delivering or transferring compounds, including, for example, S-nitrosothiols, S-nitrothiols, O-nitrosoalcohols, O-nitroalcohols, sydnonimines, 2-hydroxy-2-nitrosohydrazines (NONOates), (E)-alkyl-2-((E)-hydroxyimino)-5-nitro-3-hexene amines or amides, nitrosoamines, as well substrates for the endogenous enzymes which synthesize nitric oxide. It is contemplated that any or all of these "NO adducts" can be mono- or poly-nitrosylated or nitrosated at a variety of naturally susceptible or artificially provided binding sites for nitric oxide or derivatives which donate or release NO.

One group of such NO adducts is the S-nitrosothiols, which are compounds that include at least one —S—NO group. Such compounds include S-nitroso-polypeptides (the term "polypeptide" includes proteins and also polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars, S-nitrosylated modified and unmodified oligonucleotides (preferably of at least 5, and more particularly 5–200 nucleotides); and S-nitrosylated hydrocarbons where the hydrocarbon is a branched or straight, saturated or unsaturated, aliphatic or aromatic hydrocarbon; S-nitrosylated hydrocarbons having one or more substituent groups in addition to the S-nitroso group; and heterocyclic compounds. S-nitrosothiols and methods for preparing them are described in U.S. Pat. No. 5,380,758; Oae et al., *Org. Prep. Proc. Int.*, 15(3):165–198 (1983); Loscalzo et al., *J. Pharmacol. Exp. Ther.*, 249(3):726–729 (1989) and Kowaluk et al., *J. Pharmacol. Exp. Ther.*, 256:1256–1264 (1990), the disclosures of which are incorporated by reference herein in their entirety.

One particularly preferred embodiment of this aspect relates to S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-homocysteine, S-nitroso-cysteine and S-nitroso-glutathione.

Suitable S-nitrosylated proteins include thiol-containing proteins (where the NO group is attached to one or more sulfur groups on an amino acid or amino acid derivative thereof) from various functional classes including enzymes, such as tissue-type plasminogen activator (TPA) and cathepsin B; transport proteins, such as lipoproteins, heme proteins such as hemoglobin and serum albumin; and biologically protective proteins, such as the immunoglobulins and the cytokines. Such nitrosylated proteins are described in WO 93/09806, the disclosure of which is incorporated herein by reference in its entirety. Examples include polynitrosylated albumin where multiple thiol or other nucleophilic centers in the protein are modified.

Other suitable S-nitrosothiols include, for example:

(i) $CH_3(C(R_e)(R_f))_xSNO$ (ii) $HS(C(R_e)(R_f))_xSNO$ (iii) $ONS(C(R_e)(R_f))_xB$; and (iv) $H_2N$—$CH(CO_2H)$—$(CH_2)_x$—$C(O)NH$—$C(CH_2SNO)$—$C(O)NH$—$CH_2$—$CO_2H$ wherein x equals 2 to 20; $R_e$ and $R_f$ are as defined above; and B is a fluoro, a $C_1$–$C_6$ alkoxy, a cyano, a carboxamido, a cycloalkyl, an arylalkoxy, an alkylsulfinyl, an arylthio, an alkylamino, a dialkylamino, a hydroxy, a carbamoyl, a N-alkylcarbamoyl, a N,N-dialkylcarbamoyl, an amino, a hydroxyl, a carboxyl, a hydrogen, a nitro or an aryl.

Nitrosothiols can be prepared by various methods of synthesis. In general, the thiol precursor is prepared first, then converted to the S-nitrosothiol derivative by nitrosation of the thiol group with $NaNO_2$ under acidic conditions (pH is about 2.5) to yield the S-nitroso derivative. Acids which may be used for this purpose include aqueous sulfuric acid, acetic acid and hydrochloric acid. Alternatively, the precursor thiol may be nitrosylated by treatment with an alkyl nitrite such as tert-butyl nitrite.

Another group of such NO adducts are those wherein the compounds donate, transfer or release nitric oxide, and include compounds comprising at least one ON—O—, ON—N— or ON—C— group. The compound that includes at least one ON—N— or ON—C— group is preferably selected from the group consisting of ON—N— or ON—C-polypeptides (the term "polypeptide" includes proteins and also polyamino acids that do not possess an ascertained biological function, and derivatives thereof); ON—N— or ON—C— amino acids (including natural and synthetic amino acids and their stereoisomers and racemic mixtures); ON—N— or ON—C-sugars; ON—N— or ON—C— modified and unmodified oligonucleotides (preferably of at least 5, and more particularly 5–200 nucleotides); ON—O—, ON—N— or ON—C-hydrocarbons which can be branched or straight, saturated or unsaturated, aliphatic or aromatic hydrocarbons; ON—N— or ON—C— hydrocarbons having one or more substituent groups in addition to the ON—N— or ON—C— group; and ON—N— or ON—C-heterocyclic compounds.

Another group of such NO adducts is the nitrites which have an —O—NO group wherein the organic template to which the nitrite group is appended is a protein, polypeptide, amino acid, carbohydrate, branched or straight and saturated or unsaturated alkyl, aryl or a heterocyclic compound. A preferred example is the nitrosylated form of isosorbide. Compounds in this group form S-nitrosothiol intermediates in vivo in the recipient human or other animal to be treated and can therefore include any structurally analogous precursor R—O—NO of the S-nitrosothiols described above.

Another group of such adducts are nitrates which donate, transfer or release nitric oxide and include compounds comprising at least one $O_2N$—O—, $O_2N$—N—, $O_2N$—S— or $O_2N$—C— group. Preferred among these are those selected from the group consisting of $O_2N$—O—, $O_2N$—N—, $O_2N$—S— or $O_2N$— polypeptides; $O_2N$—O—, $O_2N$—N—, $O_2N$—S— or $O_2N$— amino acids; $O_2N$—O—, $O_2N$—N—, $O_2N$— or $O_2N$—sugars; $O_2N$—O—, $O_2N$—N—, $O_2N$—S— or $O_2N$—C— modified and unmodified oligonucleotides (preferably of at least 5, and more particularly 5–200 nucleotides); $O_2N$—O—, $O_2N$—N—, $O_2N$—S— or $O_2N$—C— hydrocarbons which can be branched or straight, saturated or unsaturated, aliphatic or aromatic hydrocarbons; $O_2N$—O—, $O_2N$—N—, $O_2N$—S— or $O_2N$—C— hydrocarbons having one or more substituent groups in addition to the $O_2N$—O—, $O_2N$—N—, $O_2N$—S— or $O_2N$—C— group; and $O_2N$—O—, $O_2N$—N—, $O_2N$—S or $O_2N$—C— heterocyclic compounds. Preferred examples are isosorbide dinitrate and isosorbide mononitrate.

Another group of such NO adducts is the nitroso-metal compounds which have the structure $(R)_u$-A-M-$(NO)_v$. R includes polypeptides (the term "polypeptide" includes proteins and also polyamino acids that do not possess an ascertained biological function, and derivatives thereof); amino acids (including natural and synthetic amino acids and their stereoisomers and racemic mixtures and derivatives thereof); sugars; modified and unmodified oligonucleotides (preferably of at least 5, and more particularly 5–200 nucleotides); and a hydrocarbon where the hydrocarbon is branched or straight, saturated or unsaturated, aliphatic or aromatic hydrocarbon; hydrocarbons having one or more substituent groups in addition to the A-nitroso group; and heterocyclic compounds. A is S, O, or N; and u and v are each independently an integer of 1, 2 or 3, and M is a metal, preferably a transition metal, including, for example, iron, copper, manganese, cobalt, selenium and lithotome. Also contemplated are N-nitrosylated metal centers such as nitroprusside.

Another group of such adducts are N-oxo-N-nitrosoamines which donate, transfer or release nitric oxide and have a $R_1R_2$—N(O-M$^+$)-NO group wherein $R^1$ and $R_2$ each independently include polypeptides, amino acids, sugars, modified and unmodified oligonucleotides, hydrocarbons where the hydrocarbon is branched or straight, saturated or unsaturated, aliphatic or aromatic hydrocarbon, hydrocarbons having one or more substituent groups and heterocyclic compounds. M$^+$ is a metal cation, such as, for example, a Group I metal cation.

Another group of such adducts are thionitrates which donate, transfer or release nitric oxide and have the structure $R_{10}-S-NO_2$ wherein $R_{10}$ is as described above by $R_1$ for the N-oxo-N-nitrosoamines.

The present invention is also directed to compounds that elevate levels of endogenous endothelium-derived relaxing factor (EDRF) and/or stimulate endogenous NO synthesis. Such compounds include, for example, L-arginine and OH-arginine. EDRF is a vascular relaxing factor secreted by the endothelium, and has been identified as nitric oxide (NO) or a closely related derivative thereof. (Palmer et al, *Nature*, 327:524–526 (1987), Ignarro et al, *Proc. Natl. Acad. Sci. USA*, 84:9265–9269 (1987))

When administered in vivo, the nitric oxides described herein may be administered in combination with pharmaceutical carriers and in dosages described herein.

In another aspect the invention provides a method of treating and/or preventing sexual dysfunctions or improving and/or enhancing sexual responses in an individual in need thereof by administering to the individual a therapeutically effective amount of a composition comprising at least one nitrosated and/or nitrosylated α-antagonist of the invention in a pharmaceutically acceptable carrier.

In another aspect the invention provides a method of treating and/or preventing sexual dysfunctions or improving and/or enhancing sexual responses in an individual in need thereof comprising administering to the individual a therapeutically effective amount of a composition comprising at least one α-adrenergic receptor antagonist (α-antagonist), which is optionally substituted with at least one NO or $NO_2$ moiety, and at least one compound that donates, transfers or releases nitric oxide or elevates levels of endogenous EDRF in a pharmaceutically acceptable carrier.

Total daily dose administered to a host in single or divided doses may be in amounts, for example, from about 1 to about 100 mg/kg body weight daily and more usually about 3 to 30 mg/kg. Dosage unit compositions may contain such amounts of submultiples thereof to make up the daily dose.

The amount of active ingredient that may be combined with the carrier materials to produce a single dosage form will vary depending upon the animal or individual treated and the particular mode of administration.

The dosage regimen for treating a disease condition with the compounds and/or compositions of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound used, whether a drug delivery system is used and whether the compound is administered as part of a drug combination. Thus, the dosage regimen actually used may vary widely and therefore may deviate from the preferred dosage regimen set forth above.

The compounds of the present invention may be administered orally, parenterally or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally used as a solvent or suspending medium. For this purpose any bland fixed oil may be used including synthetic mono- or diglycerides, in addition, fatty acids such as oleic acid find use in the preparation of injectables.

Solid dosage forms for oral administration may include capsules, tablets, pills, powders, granules and gels. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with one or more compounds which are known to be effective against the specific disease state that one is targeting for treatment. The compositions of the invention can be administered as a mixture of an α-antagonist and a nitric oxide donor, or they can also be used in combination with one or more compounds which are known to be effective against the specific disease state that one is targeting for treatment.

The invention also provides a pharmaceutical pack or kit comprising one or more containers filled with one or more of the ingredients of the pharmaceutical compositions of the invention. Associated with such kit(s) or container(s) can be a notice in the form prescribed by a governmental agency regulating the manufacture, use or sale of pharmaceuticals or biological products, which notice reflects approval by the agency of manufacture, use or sale for human administration.

EXAMPLES

The following examples are presented for illustration only, and are not intended to limit the scope of the invention or appended claims.

Example 1

N-(N-L-γ-glutamyl-S-Nitroso-L-cysteinyl) glycine

N-(N-L-γ-glutamyl-L-cysteinyl)glycine (100 g, 0.325 mol) was dissolved in deoxygenated water (200 ml) and 2N HCl (162 ml) at room temperature and then the reaction mixture was cooled to 0° C. With rapid stirring, a solution of sodium nitrite (24.4 g, 0.35 mol) in water (40 ml) was added. Stirring with cooling of the reaction mixture was continued for approximately 1 hour after which time the pink precipitate which formed was collected by vacuum filtration. The filter cake was resuspended in chilled 40% acetone-water (600 ml) and collected by vacuum filtration. The filter cake was washed with acetone (2×200 ml) and ether (100 ml) and then dried under high vacuum at room temperature in the dark to afford the title compound as a pink powder. $^1$H NMR ($D_2O$) δ: 1.98 (m, 2H), 2.32 (t, 2H), 3.67 (t, 1H), 3.82 (s 2H), 3.86 (dd, 1H), 3.98 (dd, 1H), 4.53 (m, 1H).

Example 2

2-Acyl-17α(3-methyl-3-nitrosothiolbutoxy) yohimban-16α-carboxylic Acid Methyl Ester Hydrochloride Salt 2a. 3-Methyl-3-(2-tetrahydropyranyl)thiobutyric Acid 3-Methyl-3-thiobutyric acid (4.2 g, 31 mmol), dihydropyran (2.8 ml, 31 mmol), and 200 μl of 4 N HCl/$Et_2O$ were allowed to stand at room temperature overnight. The volatiles were evaporated in vacuo (2 mm Hg) yielding 6.6 g (30 mmol) of material which was used without further purification. $^1$H-NMR ($CDCl_3$): δ 4.92 (d, J=8.1 Hz, 1H), 4.09 (d, J=10.5 Hz, 1H), 3.49–3.56 (mult, 1H), 2.73 (dd, J=1.2 and 13.7 Hz, 1H), 2.64 (d, J=13.8 Hz, 1H), 1.84–1.89 (mult 2H), 1.55–1.69 (mult, 4H), 1.51 (s, 3H), 1.42 (s, 3H).

2b. 3,3'-Methyl-3,3'(2-tetrahydropyranyl)thiobutyric Acid Anhydride

The product of Example 2a (1.1 g, 5 mmol) and triethylamine (710 μl, 5 mmol) was dissolved in ethyl acetate (50 ml) and cooled to 0° C. Triphosgene (250 mg, 0.85 mmol) was added all in one portion and the reaction was stirred at 0° C. for 15 minutes then warmed to room temperature with continued stirring for 30 min. The precipitate which formed was removed by filtration and the filtrate was concentrated by rotary evaporation to afford 1.0 g (5 mmol) of the title compound. $^1$H-NMR ($CDCl_3$): δ 5.03–5.06 (mult, 2H), 4.04–4.08 (mult, 2H), 3.46–3.51 (mult, 2H), 2.89 (d, J=15.7 Hz, 2H), 2.77 (d, J=15.6 Hz, 2H), 1.79–1.88 (mult, 4H), 1.51–1.67 (mult, 8H), 1.54 (s, 6H), 1.49 (s, 6H).

2c. 17α(3-methyl-3-tetrahydropyranylthiolbutoxy) yohimban-16α-carboxylic Acid Methyl Ester To a solution of yohimbine (1.6 g, 4.5 mmol) in pyridine (6 ml) was added the product of Example 2b (2.5 g, 6 mmol) and 4-dimethylaminopyridine (730 mg, 6 mmol). The reaction mixture was stirred at room temperature for 6 days. Acetonitrile (50 ml) was added to the reaction and then all of the volatile components were evaporated in vacuo. The residue was dissolved in ethyl acetate (100 ml) and washed with a 10% solution of aqueous sodium carbonate. The aqueous wash was then back extracted once with ethyl acetate. The combined organic extracts were washed with $H_2O$, brine, and then dried over anhydrous sodium sulfate. Treatment of the solution with activated charcoal followed by filtration and concentration of the filtrate in vacuo gave 2.8 g of a dark syrup.

Chromatography on silica gel eluting with 1:1 hexane/ethyl acetate containing 1% by volume triethylamine afforded 670 mg (20%) of the title compound. $^1$H-NMR ($CDCl_3$): δ 7.76 (s, 1H), 7.46 (d, J=7.2 Hz, 1H), 7.29 (dd, J=1.0 and 7.0 Hz, 1H), 7.12 (ddd; J=1.3, 7.1, and 7.1 Hz; 1H), 7.07 (ddd; J=1.1, 7.2, and 7.2 Hz; 1H), 5.46 (d, J=2.6 Hz, 1H), 5.07–5.11 (mult, 1H), 4.06–4.11 (mult, 1H), 3.69 (s, 3H), 3.47–3.55 (mult, 1H), 3.39 (d, J=10.4 Hz, 1H), 3.02–3.12 (mult, 2H), 2.97 (dd, J=4.5 and 12.2 Hz, 1H), 2.80 (d, J=14.3 Hz, 1H), 2.71 (mult, 1H), 2.69 (d, J=13.2 Hz, 1H), 2.61–2.65 (mult, 1H), 2.39 (dd, J=2.6 and 11.6 Hz, 1H), 2.23–2.33 (mult, 2H), 1.71–2.07 (mult, 5H), 1.58–1.69 (mult, 8H), 1.51 (s, 3H), 1.49 (s, 3H). Anal Calcd for ($C_{31}H_{42}N_2O5S$-½ $H_2O$): C66.05; H, 7.69; N, 4.97; S, 5.69. Found C, 65.74; H, 7.33; N, 4.88; S, 5.57.

2d. 2-Acyl-17α(3-methyl-3-thiolbutoxy)yohimban-16α-carboxylic Acid Methyl Ester

The product of Example 2c (620 mg, 1.1 mmol) was refluxed in a mixture of acetic acid (5 ml) and acetyl chloride (5 ml) for 4 hours. The solvent was evaporated in vacuo (2 mm Hg). The residue was partitioned between 5% aqueous ammonium hydroxide and ethyl acetate. The aqueous wash was extracted with ethyl acetate. The combined organic extracts were washed with brine and dried over anhydrous sodium sulfate. The solvent was evaporated in vacuo and the residue was chromatographed on silica gel eluting with 1:1 hexane/ethyl acetate containing 1% by volume triethylamine to afford 210 mg (34%) of 2-acyl-17u.(3-methyl-3-thioacetylbutoxy)yohimban-16α-carboxylic acid methyl ester. This diacetate (180 mg, 0.32 mmol) was dissolved in acetic acid (4 ml) to which was added mercuric trifluoroacetate (190 mg, 0.45 mmol) and the reaction mixture was stirred at room temperature for 2 hours. The volatiles were evaporated in vacuo leaving a gum which was triturated with 1N HCl (6 ml) to afford a yellow powder. The powder was partitioned between ethyl acetate and 10% aqueous ammonium hydroxide. The organic phase was filtered through Celite to remove the gray solid which was present and then the filtrate was washed with brine and then dried over anhydrous sodium sulfate.

Evaporation of the volatiles in vacuo afforded a solid which was chromatographed on silica gel eluting with a gradient of with 1:1 hexane/ethyl acetate containing 1% by volume triethylamine to ethyl acetate containing 1% by volume triethylamine to yield 60 mg (37%) of the title compound as a white powder. $^1$H-NMR ($CDCl_3$): δ 7.81 (d, J=7.0 Hz, 1H), 7.41 (d, J=6.8 Hz, 1H), 7.23–7.29 (mult, 2H), 5.46 (s, 1H), 4.17 (d, J=9.9 Hz, 1H), 3.64 (s, 3H), 3.11–3.15 (mult, 1H ), 3.00 (dd, J=3.5 and 12.4 Hz, 1H), 2.64–2.84 (mult, 10H), 2.31 (dd, J=2.6 and 11.7 Hz, 1H), 2.24 (d, J=12.7 Hz, 1H), 2.04–2.0 8 (mult, 2H), 1.41–1.62 (mult, 11H). $^{13}$C-NMR ($CDCl_3$): δ 171.6, 170.7, 169.5, 137.3, 136.4, 129.6, 124.1, 122.9, 118.3, 117.2, 114.6, 70.0, 61.0, 59.8, 51.9, 51.8, 50.9, 47.7, 45.6, 37.8, 37.6, 36.22, 36.2, 33.2, 29.9, 27.1, 23.8, 22.3.

2e. 2-Acyl-17α(3-methyl-3-nitrosothiolbutoxy)yohimban-16α-carboxylic Acid Methyl Ester Hydrochloride Salt To a slurry of the compound of Example 2d (40 mg, 0.078 mmol) in 1:1 methanol/1 N HCl (4 ML) with dimethylformamide (400 μl) was added a solution of sodium nitrite (11 mg, 0.16 mmol) in $H_2O$ (200 μl). The white powder turned green as the slurry was stirred at room temperature for 25 minutes. At this juncture dimethylformamide (600 μl) and additional aqueous sodium nitrite (11 mg in 200 μl of $H_2O$)

was added and stirring at room temperature was continued for an additional 15 minutes. The reaction mixture was partitioned between $CHCl_3$ and $H_2O$ adding 10% aqueous ammonium hydroxide to the aqueous phase until basic to pH paper. The aqueous layer was extracted with $CHCl_3$ and the combined organic extracts were washed with brine and then dried over anhydrous sodium sulfate. The volatiles were evaporated in vacuo and the residue was dissolved in ether. The product was precipitated with ethereal HCl to afford 19 mg of the title compound as a green solid. $^1$H-NMR ($CDCl_3$): δ 7.81 (dd, J=1.7 and 6.8 Hz, 1H), 7.42 (d, J=6.8 Hz, 1H), 7.23–7.29 (mult, 2H), 5.43 (d, J=2.6 Hz, 1H), 4.15 (d, J=9.8 Hz, 1H), 3.63 (s, 3H), 3.36 (d, J=15.1 Hz, 1H), 3.30 (d, J=15.1 Hz, 1H), 3.12 (dd, J=4.9 and 11.0 Hz, 1H), 3.00 (dd, J=3.7 and 12.3 Hz, 1H), 2.72 (s, 3H), 2.63–2.82 (mult, 3H), 2.31 (dd, J=2.6 and 11.7 Hz, 1H), 2.03 (s, 3H), 2.00 (s, 3H), 1.0–2.0 (mult, 9H).

Example 3

2-((β-(4(3-S-Nitroso-3-methyl-butyric Acid)phenyl)-ethyl)aminomethyl)-1-tetralone Ester Hydrochloride 3a. 2-((β-(4-Hydroxyphenyl) ethyl) t-butoxycarbonylaminomethyl)-1-tetralone 2-((β-(3-(4-Hydroxyphenyl) ethyl) aminomethyl))-1-tetralone (3.39 g, 11.5 mmol) was dissolved in dichloromethane (50 mL) and di-tert-butyldicarbonate (2.50 g, 11.5 mmol) was added. The reaction mixture was stirred for 100 minutes at room temperature. The solvent was evaporated, and the residue was purified by flash chromatography on silica-gel, eluting with hexane/ethyl acetate (3:1) to give 2.32 g (51%) of the title compound. $^1$H NMR ($CDCl_3$, 300 MHz) δ 1.44 (s, 9H), 1.61–1.89 (m, 1H), 2.15–2.29 (m, 1H), 2.50–2.85 (m, 4H), 2.90–3.08 (m, 2H), 3.29–3.45 (m,1H), 3.49–3.64 (m, 1H), 6.76 (d, 2H), 7.04 (d, 2H), 7.19–7.32 (m, 2H), 7.39–7.50(m, 1H), 8.01 (d, 1H).

3b. 2-((β-(4-(3-Tetrahydropyranylthio-3-methyl-butyric Acid)phenyl) ethyllaminomethyl)-1-tetralone Ester The product of Example 3a (0.300 g, 0.76 mmol) was dissolved in pyridine (0.5 mL) and a solution of 3,3-O-ditetrahydropyranthio-3,3-O-dimethylbutanoic anhydride (0.397 g, 0.95 mmol) in pyridine (0.5 mL) was added. The resulting solution was stirred for 18 hours at room temperature. The solvent was evaporated, and the residue was purified by flash chromatography on silica-gel, eluting with hexane/ethyl acetate (4:1) to give 0.332 g (73%) of the title compound. $^1$H-NMR ($CDCl_3$, 300 MHz) δ 1.44 (s, 9H), 1.56 (d, 6H), 1.52–1.78 (m, 6H), 1.66–1.97 (m, 1H), 2.16–2.31 (m, 1H), 2.73–3.06 (dd, overlapping with multiplet, 7H), 3.33–3.67 (m, 5H), 4.05–4.17 (m, 1H), 5.09–5.17 (m, 1H), 7.01 (d, 2H), 7.13–7.36 (m, 4H), 7.47 (t,1H), 8.01 (d, 1H).

3c. 2-((β-(4-(3-Mercapto-3-methyl-butyric Acid) phenyl) ethyl)-t-butoxycarbonylaminomethyl)-1-tetralone Ester The product of Example 3b (0.192 g, 0.32 mmol) was dissolved in methanol (2 mL) and a solution of silver nitrate (0.117 g, 0.69 mmol) in water (0.4 mL) was added. The resulting mixture was stirred for 1 hour at room temperature. The solvent was evaporated, the residue was suspended in acetone/water (1:10) and 1N HCl (1 mL) was added. After stirring for 18 hours at room temperature, the precipitate was filtered and filtrate was extracted with dichloromethane. The organic layer was washed with brine, dried over anhydrous sodium sulfate and concentrated in vacuo to give 0.085 g (51%) of the title compound. $^1$H NMR ($CDCl_3$, 300 MHz) δ 1.44 (s, 9H), 1.58 (d, 6H), 1.73–1.96 (m, 1H), 2.17–2.31 (m, 1H), 2.38 (s, 1H), 2.64–2.93 (m, 5H), 2.94–3.07 (m, 2H), 3.45 (t, 3H), 3.58–3.67 (m, 1H), 7.02 (d, 2H), 7.15–7.36 (m, 4H), 7.47 (t, 1H), 8.01 (d, 1H).

3d. 2-((β-(4-(3-Mercapto-3-methyl-butyric acid) phenyl) ethyl)-aminomethyl)-1-tetralone Ester The product of Example 3c (0.149 g, 0.29 mmol) was dissolved in dichloromethane (3 mL) and trifluoroacetic acid (3 mL) was added. The resulting solution was stirred for 15 minutes at room temperature. The solvent was evaporated and the residue was dissolved in dichloromethane (10 mL). Water (5 mL) was added and pH was made basic with saturated sodium bicarbonate solution. Organic layer was separated and aqueous fraction was extracted with dichloromethane. The combined organic phase was washed with brine, dried over anhydrous sodium sulfate and concentrated in vacuo to give 0.098 g (82%) of the title compound. $^1$H NMR ($CDCl_3$, 300 MHz) δ 159 (s, 6H), 1.84–2.03 (m, 1H), 2.15–2.26 (m, 1H), 2.39 (s, 1H), 2.82–3.16 (m, 11H), 7.06 (d, 2H), 7.18–7.35 (m, 4H), 7.49 (t, 1H), 8.00 (1H).

3e. 2-((β-(4-(3-S-Nitroso-3-methyl-butyric Acid)phenyl) ethyl) aminomethyl)-1-tetralone Ester Hydrochloride The product of Example 3d (0.081 g, 0.20 mmol) was dissolved in methanol (4 mL) and 1N HCl was added. A solution of sodium nitrite (0.045 g, 0.65 mmol) in water (0.25 mL) was added. After stirring for 15 minutes at room temperature an additional sodium nitrite (0.045 g, 0.65 mmol) in water (0.25 mL) was added. The reaction mixture was stirred for 15 more minutes, and was then extracted with dichloromethane. The organic layer was dried over anhydrous sodium sulfate and the solvent was evaporated to give 0.072 g (81%) of the title compound as a green solid. $^1$H NMR ($CDCl_3$, 300 MHz) δ 1.72–1.93 (m, 1H), 2.09 (s, 6H), 2.18–2.30 (m, 1H), 2.84–3.11 (m, 1H), 3.14–3.33 (m, 6H), 3.36–3.57 (m, 4H), 7.03 (d, 2H), 7.18–7.42 (m, 4H), 5.53 (t, 1H), 7.94 (d, 1H).

Example 4

4(2-methoxyphenyl-α-((1-napthalenyloxy)methyl)-1-piperazineethyoxy-(3-S-nitroso-3-methyl-butyric Acid) Ester 4a. 3-Methyl-3-(2,4,6-trimethoxyphenylmethylthio)butyric Acid To a solution of 3-mercapto-3-methylbutyric acid (Sweetman et al, *J. Med Chem.*, 14:868 (1971), the disclosure of which is incorporated herein by reference in its entirety) (4.6 g, 34 mmol) in methylene chloride (250 mL) under nitrogen and cooled over ice/salt to 5° C. (internal temperature) was added trifluoroacetic acid (82 g, 0.72 mol). No significant temperature rise was noted during the addition. To this was then added dropwise a solution of 2,4,6-trimethoxybenzyl alcohol (Munson et al., *J. Org. Chem.*, 57, 3013 (1992), the disclosure of which is incorporated herein by reference in its entirety) (6.45 g, 32 mmol) in methylene chloride (150 mL) such that the reaction temperature does not rise above 5° C. After the addition was complete, the mixture was stirred for an additional 5 minutes at 5° C. and the volatiles were evaporated in vacuo (toluene or ethyl acetate can be used to assist in the removal of volatile material). The residue was partitioned between diethyl ether and water and the organic phase dried over anhydrous sodium sulfate, filtered and the volatile material evaporated in vacuo. The residue was treated with activated charcoal and recrystalized from diethyl ether/hexane. The product was isolated as a white solid in 70% yield (7 g) mp 103–105° C. $^1$H NMR($CDCl_3$) δ 6.12 (s, 2H), 3.80–3.85 (m, 11H), 2.74 (s, 2H), 1.47 (s, 6H). $^{13}$C NMR ($CDCl_3$) δ 173.9, 160.6, 158.6, 105.6, 90.5, 55.7, 55.3, 45.9, 43.6, 28.4, 21.0.

4b. 4-(2-methoxyphenyl)-α-((1-naphthalenyloxy)methyl)-1-piperazineethoxy-(3-(2,4,6-trimethyoxybenzylthio)-3-methyl-butyric Acid) Ester Under a nitrogen atmosphere, 4-(2-methoxyphenyl)-⊕-((1-naphthalenyloxy)-methyl)-1-piperazineethanol (0.130 g, 0.35 mmol) was dissolved in anhydrous dimethylformamide (2 mL) and 4-dimethylaminopyridine (0.017 g, 0.14 mmol) was added, followed by the product of Example 4a (0.211 g, 0.69 mmol) and 1-ethyl-3-(3-dimethylaminopropyl)carbodiimide (0.132 g, 0.69 mmol). The resulting mixture was stirred 2 hours at room temperature and then 24 hours at 50° C. The solvent was evaporated in vacuo and the residue was purified by flash chromatography on silica gel eluting with hexane/ethyl acetate (3:1) to (2:1) to give the title compound (0. 133 g, 56% yield). $^1$H NMR (CDCl$_3$, 300 MHz) δ 1.49–1.53 (d, 6H, J=2.42 Hz). 2.70–2.84 (m, 8H), 2.98–3.09 (m, 4H), 3.75–3.85 (m, 11H), 3.86 (s, 3H), 4.31–4.36 (m, 2H), 5.43–5,52 (m, 1H), 6.08 (s, 2H), 6.81–6.86 (m, 2H), 6.90–6.93 (m. 2H), 6.97–7.01 (m, 1H), 7.33–7.7-(m, 4H), 7.77–7.82 (m, 1H), 8.23–8.27 (m, 1H).

4c. 4-(2-methoxyphenyl)-α-((1-naphthalenyloxy)methyl)-1-piperazineethoxy-(3-mercanto-3-methyl-butyric Acid) Ester The product of Example 4b (0.128 g, 0.186 mmol) was dissolved in methylene chloride (0.50 mL), and then anisole (0.13 mL, 1.20 mmol), phenol (0.013 g, 0.14 mmol), water (0.13 mL), and trifluoroacetic acid (0.80 mL, 10.4 mmol) were added. After 1 hour of stirring at room temperature, toluene (2 mL) was added and volatiles were evaporated. The residue was purified by flash chromatography on silica gel eluting with hexane/ethyl acetate (2:1) to give the title compound (0.055 g, 60% yield) as a solid. $^1$H NMR (CDCl$_3$, 300 MHz) δ 1.49–1.53 (d, 6H, J=2.42 Hz), 2.59 (s, 1H), 2.69–2.86 (m, 8H), 3.01–3.09 (m, 4H), 3.86 (s, 3H), 4.26–4.39 (m, 2H), 5.53–5.63 (m, 1H), 6.81–6.88 (d, 2H, J=7.5 Hz), 6.90–6.95 (m, 2H), 6.98–7.04 (m, 1H), 7.34–7.40 (t, 1H, J=7.5 Hz), 7.43–7.78 (m, 3H), 7.79–7.82 (m, 1H), 8.23–8.26 (m, 1H).

4d. 4-(2-methoxyphenyl)-α-((1-naphthalenyloxy)methyl)-1-piperazineethoxy-(3-S-nitroso-3-methyl-butyric Acid) Ester The product of Example 4c (0.048 g, 0.097 mmol) was dissolved in methanol (5 mL) and 1N solution of hydrochloric acid (1.5 mL) was added. The resulting mixture was cooled to 0° C. and a solution of sodium nitrite (0.040 g, 0.058 mmol) in water (0.5 mL) was added. After 1 hour stirring at 0° C. the reaction mixture was extracted with methylene chloride, washed with brine and dried over anhydrous sodium sulfate. The solvent was evaporated in vacuo to give the title compound (0.045 g, 82% yield) as a green solid. $^1$H NMR(CDCl$_3$, 300 MHz) δ 2.00 (s, 6H), 3.38–3.50 (m, 13H), 3.88 (s, 3H), 4.31–4.40 (m, 2H), 5.91 (s, 1H), 6.79–6.95 (m, 5H), 7.33–7.70 (m, 4H), 7.79–7.82 (m, 1H), 8.09–8.12 (m, 1H).

Example 5

2-(4-(2-Furoyl)piperazin-1-yl)-(4-(3-S-nitroso-3-methyl-butyric acid))-6,7-dimethyoxyquinazoline Amide 5a. 2-(4-(2-Furoyl)piperazin-1-y)-(4-(3-(2,4,6-trimethyoxybenzylthio)-3-methyl-butyric acid))-6,7-dimethyoxyquinazoline Amide Under a nitrogen atmosphere 2-(4-(2-furoyl)piperazin-1-yl)-amino-6,7-dimethyoxyquinazoline (0.200 g, 0.52 mmol) was dissolved in anhydrous dimethylformamide (5 mL) and 4-dimethylaminopyridine (0.025 g, 0.21 mmol) was added, followed by the product of Example 4a (0.319 g, 1.04 mmol) and 1-ethyl-3-(3-dimethylaminopropyl)carbodiimide (0.199 g, 1.04 mmol). The resulting mixture was stirred at 50° C. for 48 hours. The solvent was evaporated in vacuo and the residue was purified by flash chromatography on silica gel eluting with hexane/ethyl acetate (3:1) to (1:5) to give 0.072 g (20% yield) of the title compound as a white solid. $^1$H NMR (CDCl$_3$, 300 MHz) δ 1.52 (s, 6H), 2.88 (s, 1H), 2.90 (s, 2H), 2.96 (s, 1), 3.56 (s, 6H), 3.72 (s, 3H), 3.90–4.01 (m, 16H), 6.48–6.52 (dd, 1H, J=1.69 and 3.32 Hz), 6.94 (s, 1H), 7.01–7.05 (d, 1H, J=3.45 Hz), 7.19 (s, 1H), 7.50–7.53 (m, 1H).

5b. 2-(4-(2-Furoyl)piperazin-1-yl)-(4(3-mecapto-3-methyl-butyric Acid))-6,7-dimethyoxypuinazoline Amide The product of Example 5a (0.160 g, 0.24 mmol) was dissolved in methylene chloride (0.67 mL), and then anisole (0.16 mL, 1.47 mmol), phenol (0.007 g, 0.047 nimol), water (0.16 mL), and trifluoroacetic acid (0.67 mL, 8.63 mmol) were added. After 45 minutes of stirring at room temperature, toluene (5 mL) was added and volatiles were evaporated. The residue was purified by flash chromatography on silica gel eluting with methylene chloride/methanol (30:1) to (15:1) to give the title compound (0.043 g, 36% yield) as a solid. $^1$HNMR (CDCl$_3$, 300 MHz) δ 1.58 (s, 6H), 2.45 (s, 1H), 3.00 (s, 2H), 3.87–3.94 (d, 6H, J=6.28 Hz), 3.92–4.06 (m, 8H, 6.35–6.57 (dd, 1H, J=1.68 and 3.41 Hz), 6.98 (s, 1H), 7.15–7.18 (d, 1H, J=3.48 Hz), 7.49 (s, 1H), 7.54–7.59 (m, 1H).

5c. 2-(4-(2-Furoyl)piperazin-1-yl)-(4-(3S-nitroso-3-methyl-butyric Acid))-6,7-dimethyoxvqiuinazoline Amide The product of Example 5b (0.036 g, 0.080 mmol) was dissolved in methanol and 1N solution of hydrochloric acid (1 mL) was added. The resulting mixture was cooled to 0° C. and a solution of sodium nitrite (0.067 g, 0.97 mmol) in water (0.5 mL) was added. After 40 min. stirring at 0° C. the reaction mixture was extracted with methylene chloride, washed with brine and dried over anhydrous sodium sulfate. The solvent was evaporated in vacuo to give the title compound (0.023 g, 55% yield) as a green solid. $^1$H NMR (CDCl$_3$, 300 MHz) δ 2.12 (s, 6H), 3.49 (s, 2H), 3.85–3.99 (m, 14H), 6.51–6.55 (dd, 1H, J=1.74 and 3.45 Hz), 6.79–6.98 (m, 2H), 7.06–7.09 (d, 1H, J=3.23 Hz), 7.34–7.58 (m, 1H).

Example 6

4-(2-(Dimethylamino)ethoxy)-2-methyl-5-(1-methylethyl)-phenol-(3-S-nitroso-3-methyl-butyric Acid) Ester 6a. 4-(2-(Dimethylamino)ethoxy)-2-methyl-5-(1-methylethyl)phenol 4-(2-(Dimethylamino)ethoxy)-2-methyl-5-(1-methylethyl)phenol acetate ester (1.00 g, 3.20 mmol) was dissolved in methanol (10 mL) and sodium hydroxide (0.317 g, 7.92 mmol) was added. The reaction mixture was stirred at room temperature for 10 minutes, diluted with ethyl ether (10 mL) and washed with sodium bicarbonate solution. The organic layer was dried over anhydrous sodium sulfate, filtered and concentrated in vacuo to give the title compound (0.71 g, 93% yield) as a white solid. $^1$H NMR (CDCl$_3$, 300 MHz) δ 1.10–1.13 (d, 6H, J=6.9 Hz), 2.19 (s, 3H), 2.41 (s, 6H), 2.80–2.85 (t, 2H, J=3.9 Hz), 3.19–3.26 (m, 1H), 4.02–4.07 (t, 2H, J=5.9 Hz), 6.37–6.59 (d, 2H, J=3.72 Hz).

6b. 4-(2-(Dimethylamino)ethoxy)-2-methyl-5-(1-methylethyl)phenol-(3-(2,4,6-trimethyoxybenzylthio))-3-methyl-butyric Acid) Ester Under a nitrogen atmosphere, the product of Example 6a (0.270 g, 1.14 mmol) was dissolved in anhydrous dimethylformamide (2 mL) and 4-dimethylaminopyridine (0.028 g, 0.23 mmol) was added, followed by the product of Example 4a (0.418 g, 1.36 mmol) and 1-ethyl-3-(3-dimethylaminopropyl)carbodiimide (0.260 g, 1.36 mmol). The resulting mixture was stirred at 55° C. for 24 hours. The solvent was evaporated in vacuo and the residue was purified by flash chromatography on silica gel, eluting with methylene chloride/methanol (20:1) to give 0.232 g (39% yield) of the title compound. $^1$H NMR (CDCl$_3$, 300MHz) δ 1.14–1.18 (d, 6H, J=6.9 Hz), 1.59 (s, 6H), 2.15 (s, 3H), 2.35 (s, 6H), 2.72–2.77 (t, 2H, J=5.9 Hz), 2.93–2.96 (m, 2H), 3.23–3.28 (m, 1H), 3.74–4.02 (m, 11H), 4.03–4.07 (t, 2H, J=5.9 Hz), 6.11 (s, 2H), 6.67 (s, 1H), 6.81 (s, 1H).

6c. 4-(2-(Dimethylamino)ethoxy)-2-methyl-5-(1-methylethyl)phenol-(3-mercapto-3-methyl-butyric Acid) Ester The product of Example 6b (0.220 g, 0.42 mmol) was dissolved in methylene chloride (0.30 mL) and anisole (0.22 mL, 2.02 mmol), phenol (0.022 g, 0.23 mmol), water (0.22 mL) and trifluoroacetic acid (1.0 mL, 13.0 mmol) were added. After 1 hour of stirring at room temperature, toluene (5 mL) was added and volatiles were evaporated. The residue was purified by flash chromatography on silica gel, eluting with methylene chloride/methanol (20:1) to give the title compound (0.095 g, 64% yield). $^1$H NMR (CDCl$_3$, 300 MHz) δ 1.14–1.16 (d, 6H, J=6.9 Hz), 1.58 (s, 6H), 2.14 (s, 3H), 2.40 (s, 1H), 2.87–2.94 (m, 8H), 3.14–3.20 (m, 1H), 3.50–3.53 (m, 2H), 4.31–4.34 (m, 2H), 6.67 (s, 1H), 6.84 (s, 1H).

6d. 4-(2-(Dimethylamino)ethoxy)-2-methyl-5-(1-methylethyl)phenol-(3-S-nitroso-3-methyl-butyric Acid) Ester The product of Example 6c (0.035 g, 0.10 mmol) was dissolved in methanol (5 mL) and 1N solution of hydrochloric acid (1 mL) was added. The resulting mixture was cooled to 0° C. and a solution of sodium nitrite (0.014 g. 0.20 mmol) in water (0.7 mL) was added. After 20 minutes stirring at 0° C., an additional sodium nitrite (0.032 g, 0.46 mmol) in water (0.7 mL) was added and the resulting mixture was stirred for 30 minutes. The reaction mixture was extracted with methylene chloride, washed with brine and dried over anhydrous sodium sulfate. The solvent was evaporated in vacuo to afford the product (0.028 g, 67% yield) as a green solid. $^1$H NMR (CDCl$_3$, 300 MHz) δ 1.13–1.17 (d, 6H, J=6.9 Hz), 2.08–2.11 (m, 9H), 2.95 (s, 6H), 3.13–3.20 (m, 1H), 3.45–3.51 (m, 4H), 4.43–4.46 (m, 2H), 6.23 (s, 1H), 6.70 (s, 1H), 6.76 (S, 1H).

Example 7

3-((4-5-Dihydro-1-(3-S-nitroso-3-methyl butyloxy)-imidazol-2-vl)-methyl)(4-methylphenyl)amino) phenol-(3-S-nitroso-3-methyl-butyric Acid) Ester 7a. 3-Mercapto-3-methyl Butyl Acetate 3-Mercapto-3-methyl butanol (Sweetman et al, *J. Med. Chem.* 14:868 (1971), the disclosure of which is incorporated by reference herein in its entirety) (5 g, 42 mmol) and pyridine (3.6 mL, 43 mmol) were dissolved in methylene chloride (50 mL) and cooled to –78° C. Acetyl chloride (3.1 mL, 43 mmol) was added dropwise. The solution was kept cold for 30 min then allowed to warm to room temperature. Stirring was continued for 1.5 hr. The reaction mixture was diluted with methylene chloride, washed with 1 N HCl and brine, and dried over sodium sulfate. Evaporation of the solvent gave 6.6 g of the title compound which was used without further purification. $^1$H-NMR (CDCl$_3$): δ 4.25 (t, J=7.1 Hz, 2 H), 2.21 (s, 1H), 2.03 (s, 3H), 1.92 (t, J=7.2 Hz, 2H), 1.41 (s, 3H).

7b. 3-Tetrahydronpyranylthio-3-methyl Butyl Acetate

The product of Example 7a (6.6 g, 41 mmol), dihydropyran (4 mL, 44 mmol), and 4 N HCl/Et$_2$O (1 mL) were allowed to stand at room temperature for 24 hours. The volatiles were evaporated in vacuo to leave the title compound as a viscous oil which was used without further purification. $^1$H-NMR (CDCl$_3$): δ 4.97 (dd, J=3.4 and 6.6 Hz, 1H), 4.24 (t, J=7.1 Hz, 2H), 4.04–4.09 (mult, 1H), 3.46–3.52 (mult, 1H), 2.03 (s, 3H), 1.93 (t, J=7.5 Hz, 2H), 1.42–1.88 (mult, 6H), 1.37 (s, 3H), 1.36 (s, 3H).

7c. 3-Tetrahydropyranylthio-3-methyl Butanol

The product of Example 7b (800 mg, 3.3 mmol) and sodium bicarbonate (1.4 g, 16 mmol) were dissolved in methanol (10 mL) and stirred at room temperature for 18 hours. The reaction mixture was diluted with ether (30 mL) to precipitate the salts and filtered through Celite. Evaporation of the solvent and chromatography on silica gel eluting with 3:1 hexane/ethyl acetate gave 340 mg (51%) of the title compound. $^1$H NMR (CDCl$_3$): δ 4.92 (dd, J=3.1 and 7.6 Hz, 1H), 4.05 (ddd; J=4.0, 4.0, and 11.6 Hz, 1H), 3.81 (ddd; J=6.3, 6.3, and 12.6 Hz, 1H), 3.78 (ddd; J=6.3, 6.3 and 12.6 Hz, 1H), 3.49 (ddd; J=3.8, 7.7, and 11.8 Hz, 1H), 1.79–1.89 (mult, 4H), 1.60–1.67 (mult, 4H), 1.56 (s, 3H), 1.55 (s, 3H). Anal calcd for $C_{10}H_{20}O_2S$: C; 58.78 H; 9.87, S; 15.69. Found C; 58.42, H; 9.73, S; 15.58.

7d. 3-((4,5-Dihydro-1-(3-tetrahydropyranylthio-3-methyl butyloxy)-imidazol-2-yl)methyl)amino]phenol-(3-tetrahydropyranylthio-3-methyl-butyric Acid) Ester The product of Example 7c (700 mg, 3.5 mmol) was dissolved in tetrahydrofuran (5 mL) and cooled to –78° C. To this solution was added 2.5 M BuLi (1.38 mL, 3.5 mmol), and the reaction mixture was stirred at –78° C. for 20 minutes. A solution of 1.93 M phosgene in toluene (3.6 mL, 7.0 mmol) was cooled to –78° C. and the cold solution of lithium alkoxide was rapidly cannulated into the phosgene solution. The reaction mixture was stirred at –78° C. for 30 minutes and then warmed to room temperature and stirred for 2 hours. The solution was filtered through a cotton plug and concentrated to give the chloroformate as a syrup. A slurry of 3-((4,5-dihydro-1H-imidazol-2-yl)methyl)(4-methylphenyl)amino)phenol hydrochloride (500 mg, 1.6 mmol) and triethylamine (650 µL, 4.7 mmol) in methylene chloride (10 mL) was cooled to –78° C. The chloroformate was dissolved in methylene chloride (4 mL) and this solution was added to the slurry. The resulting reaction mixture was stirred at –78° C. for 30 minutes and was then warmed to room temperature and stirred for 20 hours. The reaction mixture was diluted with methylene chloride and then washed successively with 0.1 N HCl, saturated aqueous sodium bicarbonate, and brine; followed by drying over sodium sulfate. Evaporation of the solvent and chromatography on silica gel eluting with 2:1 hexane/ethyl acetate gave 540 mg (46%) of the title compound. $^1$H NMR (CDCl$_3$): δ 7.18 (d, J=8.6 Hz, 2H), 7.13 (d, J=8.0 Hz, 2H), 7.12 (t, J=8.2 Hz. 1H), 6.57–6.62 (mult, 2H), 6.51 (t, J=2.2 Hz, 1H), 4.94–4.99 (mult. 2 H), 4.89 (s, 2H), 4.38 (t, J=7.3 Hz, 2H), 4.32 (t, J=7.1 Hz, 2H), 4.03–4.08 (mult, 2 H), 3.79 (s, 4H), 3.46–3.52 (mult, 2H), 2.32 (s, 3H), 1.51–2.05 (mult, 16H).

7e. 3-((4,5-Dihydro-1-(3-thiol-3-methyl butyloxy)-imidazol-2-yl)methyl)(4-methylphenyl)amino)phenol-(3-thiol-3-methyl-butyric Acid) Ester The product of Example 7d (400 mg, 0.54 mmol), mercaptoethanol (760 µL, 10 mmol), and 4 N HCl in ether (250 µL, 1 mmol) were kept at room temperature for 24 hours. The reaction mixture was diluted with ethyl acetate and then washed with saturated aqueous sodium bicarbonate, water, and brine, and then dried over sodium sulfate. Hydrochloric acid was added and the solvent was evaporated to leave a syrup. The syrup was triturated with ethanol and ether. Decantation of the solvents and subjecting the residue to high vacuum overnight afforded 130 mg of solid. The solid was chromatographed on silica gel eluting with 3:1 hexane/ethyl acetate to give 30 mg (10%) of the title compound. $^1$H NMR (CDCl$_3$): δ 7.18 (d, J=8.6 Hz, 2H), 7.14 (d, J=7.9 Hz, 2H), 7.13 (t, J=8.2 Hz, 1H), 6.61 (dd, J=2.4 and 8.3 Hz, 1H), 6.59 (dd, J=2.1 and 7.9 Hz, 1H), 6.52 (t, J=2.2 Hz, 1H), 4.90 (s, 2H), 4.41 (t, J=7.3 Hz, 2H), 4.35 (t, J=7.0 Hz, 2H), 3.80 (s, 4H), 2.33 (s, 3H), 2.02 (t, J=7.1 Hz, 2H), 1.97 (t, J=7.1 Hz, 2H), 1.76 (s, 1H), 1.75 (s, 1H), 1.43 (s, 12H).

7f. 3-((4,5-Dihydro-1-(3-S-nitroso-3-methyl butyloxy)-imidazol-2-yl)methyl) (4-methylphenyl)amino)phenol-(3-S-nitroso-3-methyl-butyric Acid) Ester The product of Example 7e (18 mg, 0.033 mmol) was dissolved in dimethylformamide (200 μL) and 4 N HCl in ether (25 μL, 0.1 mmol) was added. The reaction mixture was cooled to 0° C. and tert-butyl nitrite (12 μL, 0.12 mmol) was added and then the reaction mixture was stirred at for 0° C. for 20 minutes. The solvent was evaporated in vacuo and the solid residue obtained was azetroped with chloroform to afford the title compound as a foam. $^1$H NMR (DMSO-d$_6$): δ 7.09 (d J=8.0 Hz, 1H), 6.89 (d, J=8.2 Hz, 1H), 6.61–6.72 (mult, 6H) 5.10 (br s, 2H), 4.44 (t. J=6.7 Hz, 2H), 4.38 (t, J=6.7 Hz, 2H), 4.00–4.10 (mult, 2H), 3.89–4.00 (mult, 2H), 2.65 (t, J=6.5 Hz, 2H), 2.62 (t, J=6.6 Hz, 2H), 2.30 (s, 3H), 1.92 (s, 6H), 1.89 (s, 6H).

Example 8

4(2-(Dimethylamino)ethoxy)-2-methyl-5-(1-methylethyl)phenol-(4-(2-nitrosothiolcyclohexylmethylamido)) Butyric Acid Ester Hydrochloride 8a. 4-(2-(Dimethylamino)ethoxy)-2-methyl-5-(1-methylethyl)phenol-(4-carboxylic Acid) Butyric Acid Ester The product of Example 6a was dissolved in anhydrous chloroform (32 mL) and glutaric anhydride (0.886 g, 7.77 mmol) was added, followed by DMAP (0.190 g, 1.56 mmol) and triethylamine (0.820 mL, 5,84 mmol). The resulting mixture was stirred at 55° C. for 42 hours. The mixture was cooled down to room temperature and poured into dichloromethane/water mixture. The organic fraction was separated, washed with brine, dried over anhydrous sodium sulfate and concentrated in vacuo to give (1.42 g, 94% yield) of the title compound as a clear oil. $^1$H NMR (300 MHz, CDCl$_3$) δ 1.13–1.18 (d, 6H), 2.04 (s, 3H), 2.04–2.13 (m, 2H), 2.38–2.44 (t, 2H), 2.50 (s, 6H), 2.60–2.66 (t, 2H), 2.96–3.07 (t, 2H), 3.17–3.26 (m, 1H), 4.11–4.16 (t, 2H), 6.65 (s, 1H), 6.79 (s, 1H).

8b. 4-(2-Dimethylamino)ethoxy)-2-methyl-5-(1-methylethyl)phenol-(4-(2-mercaptocyclohexylmethylamido)) Butyric Acid Ester Under a nitrogen atmosphere, the product of Example 8a (1.4 g, 3.62 mmol) was dissolved in anhydrous chloroform (20 mL) and 2-mercaptocyclohexylmethylamine (0.71 g, 4.8 mmol) was added, followed by DMAP (0.195 g, 1.6 mmol). A solution of EDAC (0.764 g, 4.00 mmol) in chloroform (10 mL) was added dropwise and the resulting mixture was stirred at 55° C. for 40 hours. Volatiles were evaporated and the residue was purified by chromatography on silica-gel, eluting with methylene chloride/methanol (15:1) to give (0.930 g, 54% yield) of the title compound as a clear oil. $^1$H NMR (300 MHz, CDCl$_3$) δ 1.13–1.18 (d, 6H), 1.42–1.68 (m, 10H), 2.10 (s, 3H), 2.10–2.13 (m, 2H), 2.36 (s, 6H), 2.34–2.38 (m, 2H), 2.61–2.66 (t, 2H), 2.72–2.78 (t, 2H), 3.17–3.26 (m, 1H), 3.39–3.43 (d, 2H), 4.02–4.07 (t, 2H), 6.05 (s, 1H), 6.66 (s, 1H), 6.79 (s, 1H).

8c. 4-(2-(Dimethylamino)ethoxy)-2-methyl-5-(1-methylethyl)phenol-4(2-nitrosothiolcyclohexylmethylamido) Butyric Acid) Ester Hydrochloride The product of Example 8b (0.285 g, 0.60 mmol) was dissolved in dichloromethane (9 mL) and 2.9 N HCl in ether (0.06 mL) was added. The resulting mixture was cooled to 0° C. and tert-butyl nitrite (0.300 mL, 2.53 mmol) was added, followed by 2.9 NHCl in ether (0.05 mL). The reaction mixture was stirred on ice for 45 minutes and volatiles were evaporated. The residue was purified by chromatography on silica-gel, eluting with methylene chloride/methanol (15:1) to give the green solid. The solid was dissolved in methylene chloride/ether and treated with 2.9 N HCl in ether (0.200 mL). Volatiles were evaporated under reduced pressure to give (0.164 g, 50% yield) of the title compound as a green solid. $^1$H NMR (300 MHz, CDCl$_3$) δ 1.14–1.18 (d, 6H), 1.47–1.55 (m, 3H), 1.71–1.77 (m, 3H), 2.02–2.09 (m, 7H), 2.27–2.34 (t, 2H), 2.41–2.50 (m, 2H), 2.57–2.74 (t, 2H), 2.74 (s, 6H), 3.17–3.26 (m, 3H), 4.14–4.18 (d, 2H), 4.30–4.34 (t, 2H), 5.75 (s, 1H), 6.68 (s, 1H), 6.8 (s, 1H).

Example 9

In Vivo Comparative Erectile Responses

Male New Zealand white rabbits weighing 2.5 kg were used as the animal model. Animals were first relaxed with an i.m. injection of 25 mg/kg ketamine prior to anesthesia with a bolus i.v. injection of 10 mg/kg Profol and maintained with i.v. infusion at 0.5 mg/kg/min. Ventilation of the animals was performed with 1% halothane plus 0.8 L/min O$_2$ and 1 L/min N$_2$O. A 22 gauge angiocatheter was placed in the femoral artery for measurement of systemic blood pressure. A dorsal incision was made in the penis and the corpora cavernosa exposed and cannulated with a 21 gauge butterfly needle to measure intracavernosal pressure.

Drugs at various concentrations were delivered intracavernosally at a volume of 150 μl through a 25 gauge needle. A 150 μl solution of a mixture of papaverine (30 mg/kg), phentolamine (1 mg/kg) and prostaglandin E1 (10 μg/ml) (pap/phent/PGE1) was injected in the corpora as a standard solution for comparison with the response of yohimbine, Example 1, Example 2, and the combination of yohimbine and Example 1. This pap/phent/PGE1 mixture is considered to cause a maximal erection-inducing effect.

Figure 2:
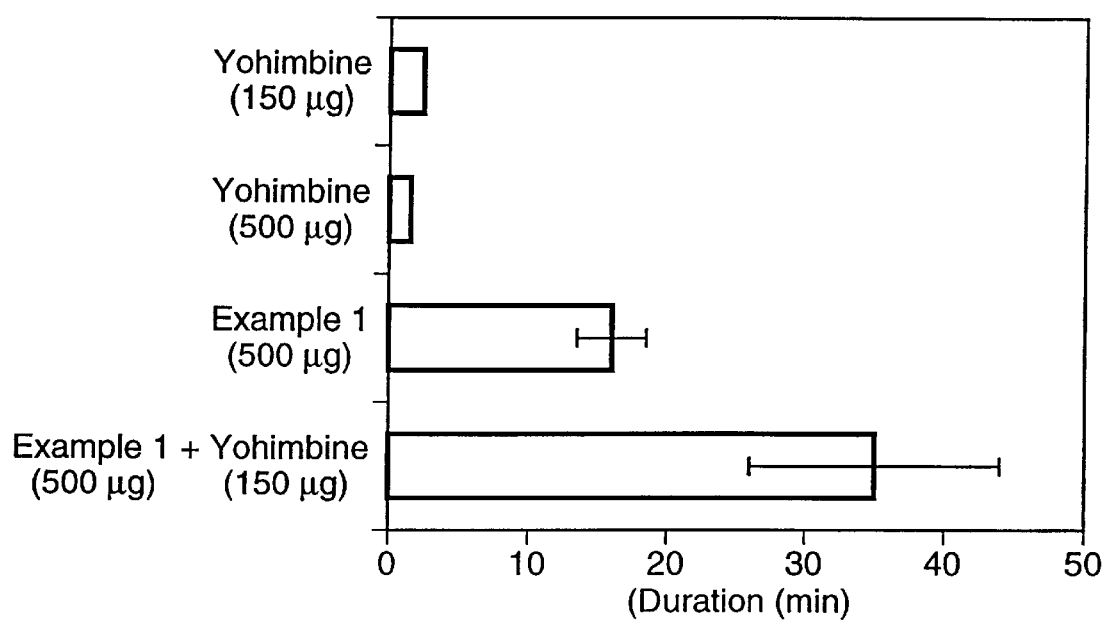
FIG. 2 shows the duration of the erectile response in vivo in the anesthetized rabbit upon intracavernosal administration of yohimbine (150 μg, 500 μg), Example 1 (500 μg), and a combination of yohimbine (150 μg) and Example 1 (500 μg). The ordinate indicates the various drugs given and the abscissa is the duration in minutes.

As shown in FIG. 1, yohimbine dose dependently induced erectile response in the anesthetized rabbit. A 500 μg dose of Example 1 was able to induce near maximal response relative to the standard dose of pap/phent/PGE1. A combination of the submaximal dose of yohimbine (150 μg) and Example 1 (500 μg) also induced maximum erectile response. Yohimbine at both the submaximal and maximal efficacy doses produced very short duration of action (FIG. 2). Example 1 produced a much longer duration of action. The duration of action is potentiated by a combination of Example 1 and yohimbine which is longer than the sum of the duration of each of these compounds alone (FIG. 2).

Figure 3:
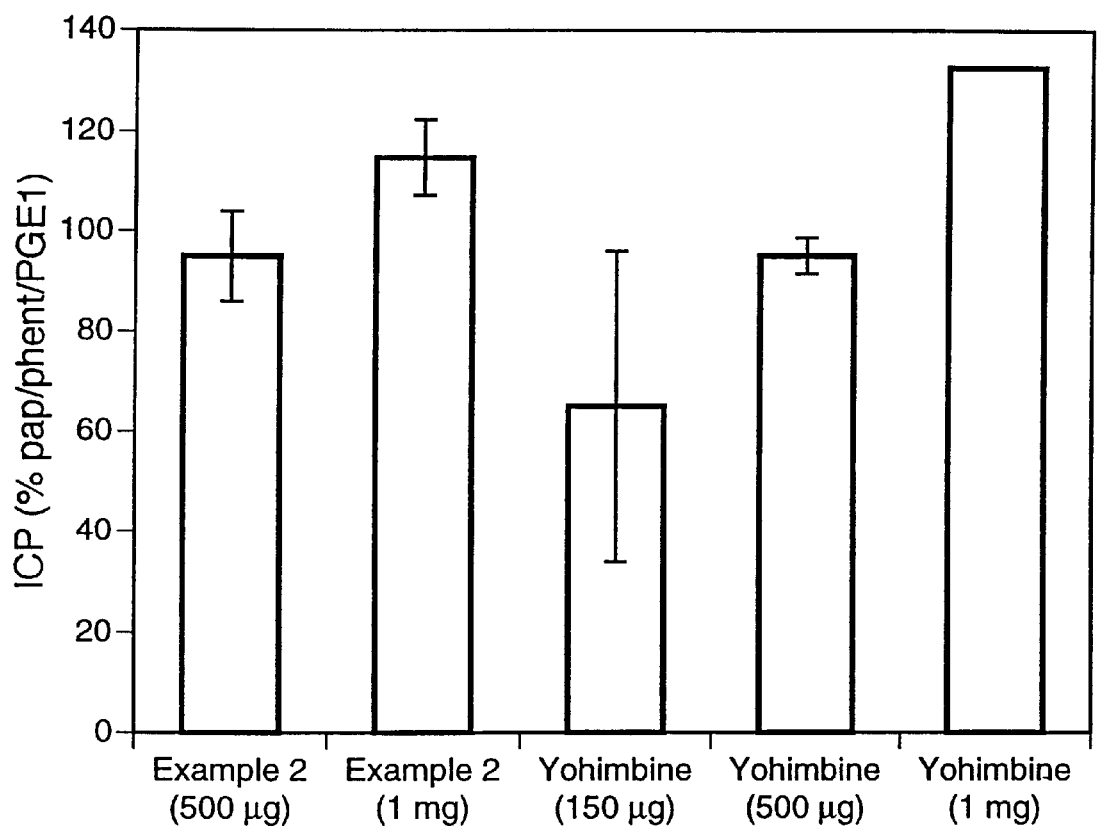
FIG. 3 shows the percent peak erectile response in vivo compared to that produced by 150 μl of pap/phent/PGE1 (30 mg/ml: 1 mg/ml: 10 μg/ml) in the anesthetized rabbit following the intracavernosal injection of 150 ul of yohimbine (150 μg, 500 μg and 1 mg) and Example 2 (500 μg, 1 mg). The ordinate is the percent response of intracavernosal pressure relative to that produced by pap/phent/PGE1 and the abscissa indicates the various doses of yohimbine and Example 2 given.
Figure 4:
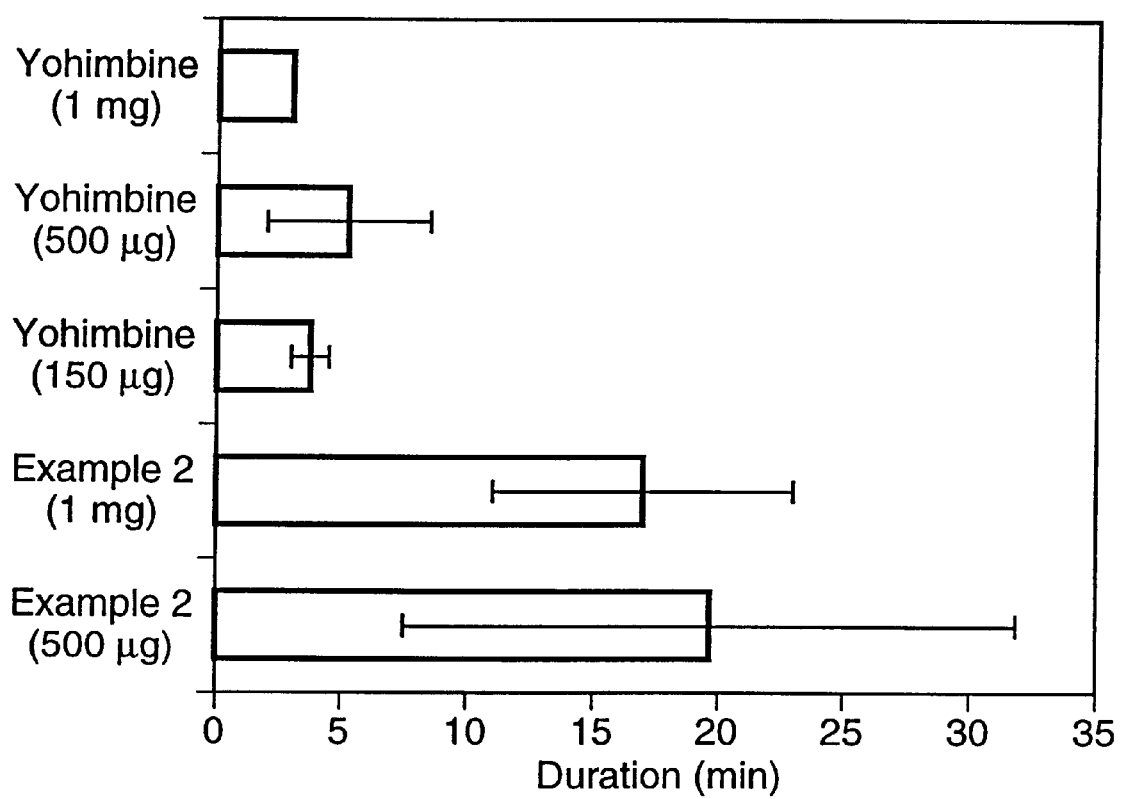
FIG. 4 shows the duration of the erectile response in vivo in the anesthetized rabbit upon intracavernosal administration of yohimbine (150 μg, 500 μg and 1 mg) and Example 2 (500 μg and 1 mg). The ordinate indicates the various doses of yohimbine and Example 2 given and the abscissa is the duration in minutes.
Figures 5A, 5B:
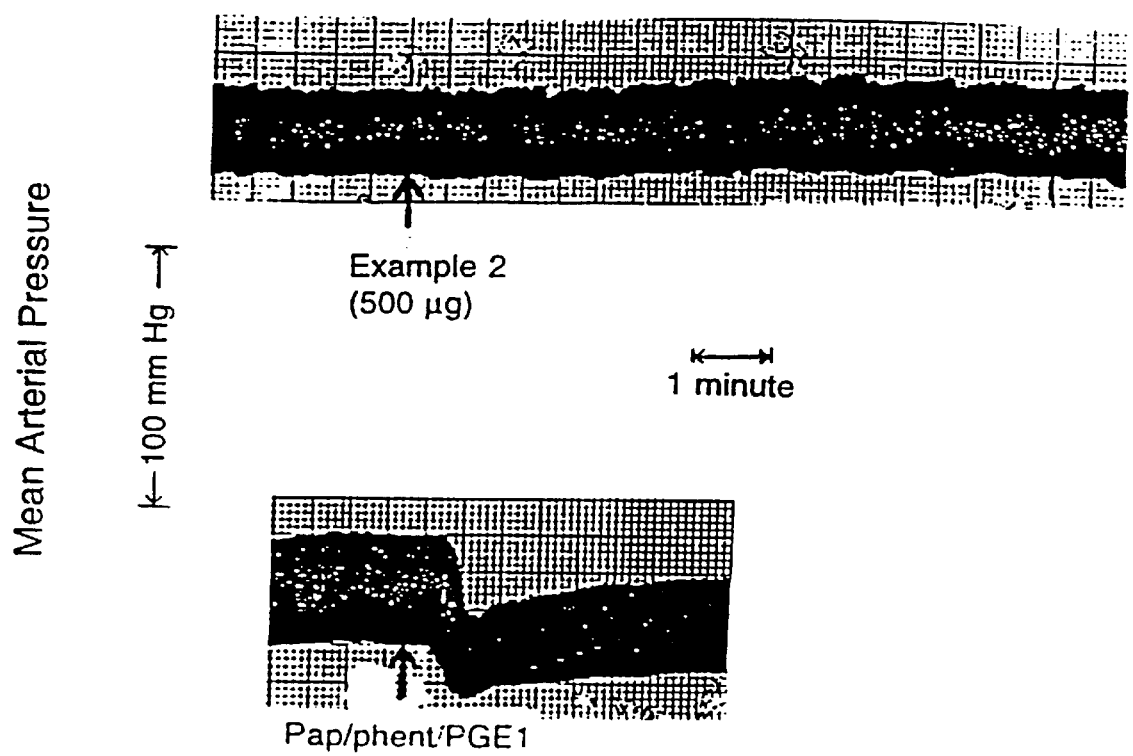
FIG. 5A shows the effects of intracavernosal injections of Example 2 (500 μg) on systemic blood pressure in the anesthetized rabbit. For comparison.
FIG. 5B shows the effects of intracavernosal injections of the standard mixture of pap/phent/PGE1 on systemic blood pressure in the anesthetized rabbit.

FIG. 3 shows that the compound of Example 2 at the 500 ug dose is equipotent to the standard dose of pap/phent/PGE1. A higher dose of the compound of Example 2 (1 mg) is at least equal to or more efficacious than the standard dose of the pap/phent/PGE1 mixture. FIG. 4 shows that the compound of Example 2 has the advantage of producing longer duration of action compared to yohimbine. FIG. 5A demonstrates that a dose (500 µg) of the compound of Example 2 effective in the erectile response did not produce any effect on systemic blood pressure upon intracavernosal injection. However, FIG. 5B demonstrates that a standard dose of the mixture of pap/phent/PGE1 produced a significant decrease in systemic blood pressure upon intracavernosal injection, suggesting that the compound of Example 2 lacks this side effect.

Figure 6:
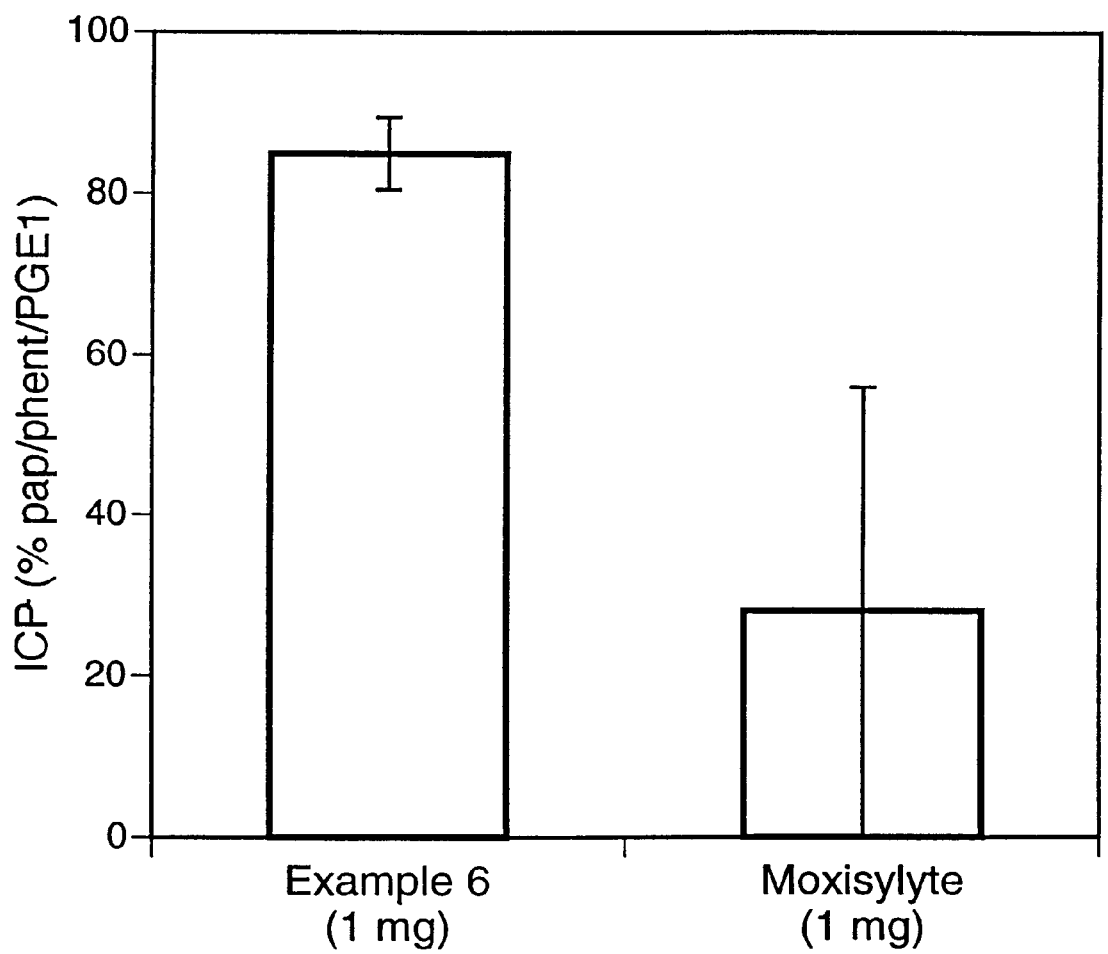
FIG. 6 shows the percent peak erectile response in vivo compared to that produced by 150 μl of pap/phent/PGE1 (30 mg/ml: 1 mg/ml: 10 μg/ml) in the anesthetized rabbit following the intracavernosal injection of moxisylyte (1 mg) and Example 6 (1 mg). The ordinate is the percent response of intracavernosal pressure relative to that produced by pap/phent/PGE1 and the abscissa indicates the dose of moxisylyte and Example 6 given.
Figure 7:
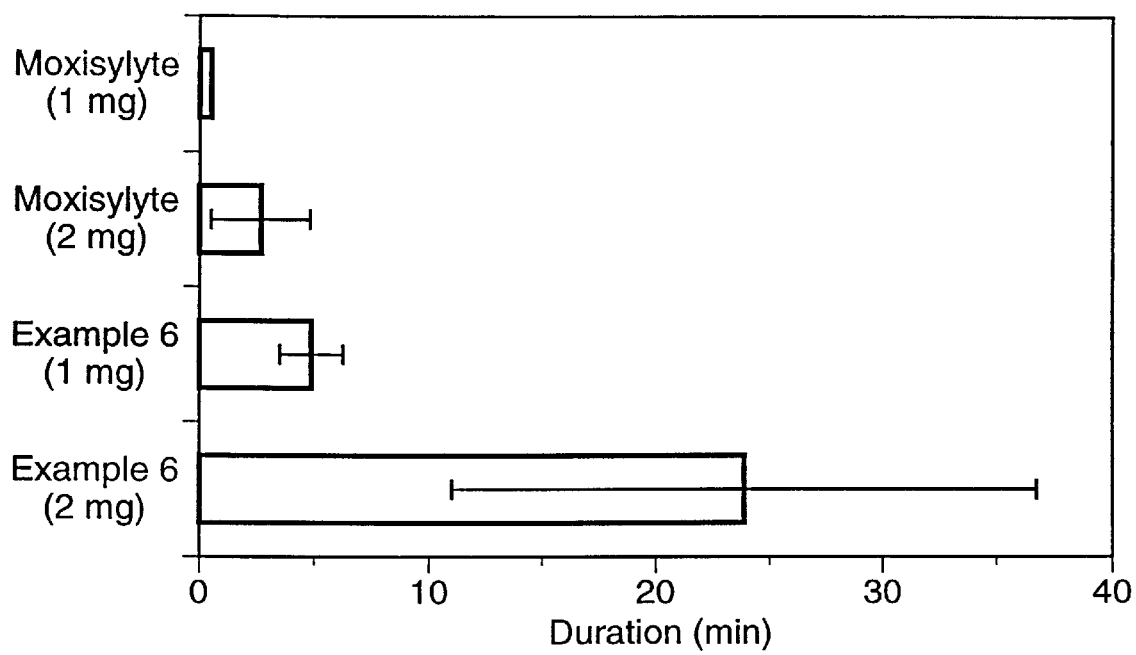
FIG. 7 shows the duration of the erectile response in vivo in the anesthetized rabbit upon intracavernosal administration of moxisylyte (1 and 2 mg) and Example 6 (1 and 2 mg). The ordinate indicates the dose of moxisylyte and Example 6, and the abscissa is the duration in minutes.

FIG. 6 shows that intracavernosal administration of 1 mg of Example 6 is more efficacious than 1 mg moxisylyte in inducing the erectile response in vivo in the anesthetized rabbit. FIG. 7 shows that a 1 mg dose of Example 6 produces a longer duration of erectile response compared to 1 mg moxisylyte. Also, FIG. 7 shows that 2 mg of Example 6 produces a much longer duration of action compared to 2 mg moxisylyte.

FIG. 1 shows the percent peak erectile response in vivo compared to that produced by 150 µl of pap/phent/PGE1 (30 mg/ml: 1 mg/ml: 10 µg/ml) in the anesthetized rabbit following the intracavernosal injection of 150 l of yohimbine (150 µg, 500 µg), the compound of Example 1 (500 µg), and a combination of yohimbine (150 µg) and the compound of Example 1 (500 µg). The ordinate is the percent response of intracavernosal pressure relative to that produced by pap/phent/PGE1 and the abscissa indicates the various drugs given.

FIG. 2 shows the duration of the erectile response in vivo in the anesthetized rabbit upon intracavernosal administration of yohimbine (150 µg, 500 µg), the compound of Example 1 (500 µg), and a combination of yohimbine (150 µg) and the compound of Example 1 (500 µg). The ordinate indicates the various drugs given and the abscissa is the duration in minutes.

FIG. 3 shows the percent peak erectile response in vivo compared to that produced by 150 µl of pap/phent/PGE1 (30 mg/ml: 1 mg/ml: 10 µg/ml) in the anesthetized rabbit following the intracavernosal injection of 150 µl of yohimbine (150 µg, 500 µg and 1 mg) and the compound of Example 2 (500 µg, 1 mg). The ordinate is the percent response of intracavernosal pressure relative to that produced by pap/phent/PGE1 and the abscissa indicates the various doses of yohimbine and the compound of Example 2 given.

FIG. 4 shows the duration of the erectile response in vivo in the anesthetized rabbit upon intracavernosal administration of yohimbine (150 µg, 500 jig and 1 mg) and the compound of Example 2 (500 µg and 1 mg). The ordinate indicates the various doses of yohimbine and the compound of Example 2 given and the abscissa is the duration in minutes.

FIG. 5A shows the effects of intracavernosal injections of Example 2 (500 µg) on systemic blood pressure in the anesthetized rabbit. For comparison, FIG. 5B shows the effects of intracavernosal injections of the standard mixture of pap/phent/PGE1 on systemic blood pressure in the anestized rabbit.

FIG. 6 shows the percent peak erectile response in vivo compared to that produced by 150 µl of pap/phent/PGE1 (30 mg/ml: 1 mg/ml; 10 µg/ml) in the anesthetized rabbit following the intracavernosal injection of moxisylyte (1 mg) and the compound of Example 6 (1 mg). The ordinate is the percent response of intracavernosal pressure relative to that produced by pap/phent/PGE1 and the abscissa indicates the dose of moxisylyte and the compound of Example 6 given.

FIG. 7 shows the duration of the erectile response in vivo in the anesthetized rabbit upon intracavernosal administration of moxisylyte (1 and 2 mg) and the compound of Example 6 (1 and 2 mg). The ordinate indicates the dose of moxisylyte and the compound of Example 6, and the abscissa indicates the duration in minutes.

Each of the publications, patents and patent applications described herein is hereby incorporated by reference herein in their entirety.

Various modifications of the invention, in addition to those described herein, will be apparent to one skilled in the art from the foregoing description. Such modifications are also intended to fall within the scope of the appended claims.

What is claimed is:

1. A composition comprising an imidazoline α-adrenergic receptor antagonist, wherein the imidazoline α-adrenergic receptor antagonist is phentolamine, tolazoline, idazoxan, deriglidole, RX 821002, BRL 44408 or BRL 4409, and a compound that stimulates nitric oxide synthesis.

2. The composition of claim 1, wherein the compound that stimulates nitric oxide synthesis is L-arginine or OH-arginine.

3. The composition of claim 1, wherein the composition is in an orally administrable form.

4. The composition of claim 1, wherein the composition is in a topically administrable form.

5. The composition of claim 1, wherein the composition is in a form administrable by injection.

6. The composition of claim 1, further comprising a pharmaceutically acceptable carrier.

7. A kit comprising the composition of claim 1.

8. The kit of claim 7, further comprising a pharmaceutically acceptable carrier.

9. A method of treating a sexual dysfunction in an individual in need thereof comprising administering to the individual the composition of claim 1 in a pharmaceutically acceptable carrier.

10. The method of claim 9, wherein the individual is female.

11. The method of claim 9, wherein the individual is male.

12. The method of claim 9, wherein the composition is administered orally.

13. The method of claim 9, wherein the composition is administered topically.

14. The method of claim 9, wherein the composition is administered by injection.

15. A composition comprising phentolamine and L-arginine.

16. The composition of claim 15, wherein the composition is in an orally administrable form.

17. The composition of claim 16, wherein the orally administrable form is a solid dosage form.

18. The composition of claim 17, wherein the solid dosage form is a powder.

19. The composition of claim 16, wherein the orally administrable form is a liquid dosage form.

20. The composition of claim 19, wherein the liquid dosage form is a solution, a suspension or an emulsion.

21. The composition of claim 15, wherein the composition is in a topically administrable form.

22. The composition of claim 15, wherein the composition is in a form that is administrable by injection.

23. The composition of claim 15, further comprising a pharmaceutically acceptable carrier.

24. A kit comprising the composition of claim 15.

25. The kit of claim 24, further comprising a pharmaceutically acceptable carrier.

26. A kit comprising phentolamine and L-arginine.

27. The kit of claim 26, wherein phentolamine and L-arginine are separate components in the kit.

28. A method of treating a sexual dysfunction in an individual in need thereof comprising administering to the individual the composition of claim 15 in a pharmaceutically acceptable carrier.

29. The method of claim 28, wherein the individual is female.

30. The method of claim 28, wherein the individual is male.

31. The method of claim 28, wherein the composition is administered orally.

32. The method of claim 31, wherein the composition is administered orally in a liquid dosage form.

33. The method of claim 32, wherein the liquid dosage form is a solution, a suspension or an emulsion.

34. The method of claim 31, wherein the composition is administered orally in a solid dosage form.

35. The method of claim 34, wherein the solid dosage form is a powder.

36. The method of claim 28, wherein the composition is administered topically.

37. The method of claim 29, wherein the composition is administered topically to the female.

38. The method of claim 28, wherein the composition is administered by injection.

39. A method of treating a sexual dysfunction in an individual in need thereof comprising administering phentolamine and L-arginine.

40. The method of claim 39, wherein the individual is male.

41. The method of claim 39, wherein the individual is female.

42. The method of claim 39, wherein the phentolamine and L-arginine are administered separately.

43. A kit comprising an imidazoline α-adrenergic receptor antagonist, wherein the imidazoline α-adrenergic receptor antagonist is phentolamine, tolazoline, idazoxan, deriglidole, RX 821002, BRL 44408 or BRL 4409, and a compound that stimulates nitric oxide synthase.

44. The kit of claim 43, wherein the imidazoline α-adrenergic receptor antagonist and the compound that stimulates nitric oxide synthase are separate components in the kit.

45. The kit of claim 43, wherein the compound that stimulates nitric oxide synthesis is L-arginine or OH-arginine.

46. A method of treating a sexual dysfunction in an individual in need thereof comprising administering an imidazoline α-adrenergic receptor antagonist, wherein the imidazoline α-adrenergic receptor antagonist is phentolamine, tolazoline, idazoxan, deriglidole, RX 821002, BRL 44408 or BRL 4409, and a compound that stimulates nitric oxide synthase.

47. The method of claim 46, wherein the individual is male.

48. The method of claim 46, wherein the individual is female.

49. The method of claim 46, wherein the imidazoline α-adrenergic receptor antagonist and the compound that stimulates nitric oxide synthase are administered separately.

50. The method of claim 46, wherein the compound that stimulates nitric oxide synthesis is L-arginine or OH-arginine.

* * * * *